(12) United States Patent
Merrill

(10) Patent No.: US 8,353,942 B2
(45) Date of Patent: Jan. 15, 2013

(54) COOLING GUIDE CATHETER AND ASSOCIATED METHOD OF USE

(76) Inventor: Thomas Lad Merrill, Sewell, NJ (US)

( * ) Notice: Subject to any disclaimer, the term of this patent is extended or adjusted under 35 U.S.C. 154(b) by 0 days.

(21) Appl. No.: 13/188,640

(22) Filed: Jul. 22, 2011

(65) Prior Publication Data

US 2011/0276115 A1 Nov. 10, 2011

Related U.S. Application Data

(63) Continuation-in-part of application No. 11/226,683, filed on Sep. 14, 2005, now abandoned.

(60) Provisional application No. 60/610,333, filed on Sep. 16, 2004, provisional application No. 60/650,297, filed on Jan. 26, 2005.

(51) Int. Cl.
*A61F 7/12* (2006.01)

(52) U.S. Cl. .......................... 607/105; 607/104; 607/106

(58) Field of Classification Search ........... 607/104–106
See application file for complete search history.

(56) References Cited

U.S. PATENT DOCUMENTS

| | | | |
|---|---|---|---|
| 5,180,364 A | 1/1993 | Ginsburg | |
| 5,531,721 A | 7/1996 | Pepin et al. | |
| 6,033,383 A | 3/2000 | Ginsburg | |
| 6,096,068 A | 8/2000 | Dobak et al. | |
| 6,124,684 A | 9/2000 | Sievers | |
| 6,231,594 B1 | 5/2001 | Dae | |
| 6,375,674 B1 | 4/2002 | Carson | |
| 6,497,721 B2 * | 12/2002 | Ginsburg et al. | 607/106 |
| 6,527,798 B2 * | 3/2003 | Ginsburg et al. | 607/106 |
| 6,607,517 B1 * | 8/2003 | Dae et al. | 604/500 |
| 6,620,188 B1 * | 9/2003 | Ginsburg et al. | 607/106 |
| 6,645,234 B2 | 11/2003 | Evans et al. | |
| 7,018,399 B2 | 3/2006 | Dobak, III et al. | |
| 7,172,586 B1 * | 2/2007 | Dae et al. | 604/500 |
| 7,211,066 B1 | 5/2007 | Merrill | |
| 7,217,282 B2 * | 5/2007 | Ginsburg et al. | 607/96 |
| 7,494,504 B2 * | 2/2009 | Ginsburg et al. | 607/113 |
| 7,771,460 B2 * | 8/2010 | Ginsburg et al. | 607/96 |
| 2001/0005791 A1 | 6/2001 | Ginsburg et al. | |
| 2001/0047196 A1 * | 11/2001 | Ginsburg et al. | 607/96 |
| 2006/0058859 A1 * | 3/2006 | Merrill | 607/105 |
| 2007/0233212 A1 * | 10/2007 | Ginsburg et al. | 607/106 |
| 2008/0228141 A1 * | 9/2008 | Ginsburg et al. | 604/113 |
| 2011/0275935 A1 * | 11/2011 | Ginsburg et al. | 600/433 |

OTHER PUBLICATIONS

Lampe et al., Rapid cooling saves lives: a bioengineering opportunity, Expert Reviews of Medical Devices, Jul. 2007, vol. 4, No. 4, pp. 441-446.

(Continued)

*Primary Examiner* — Roy Gibson
*Assistant Examiner* — Kaitlyn Smith
(74) *Attorney, Agent, or Firm* — Polster Lieder Woodruff & Lucchesi, L.C.

(57) ABSTRACT

A catheter apparatus configured to provide a delivery system for standard intervention devices typically used during emergency angioplasty and to provide rapid localized cooling to organs at risk of ischemic and reperfusion injury. The catheter apparatus including a catheter shaft having an inner core defining at least two coolant flow lumens adjacent to a blood conveyance lumen. Each coolant flow lumen in thermal contact with the blood conveyance lumen and thermally insulated from each other and the exterior surfaces of the catheter shaft.

20 Claims, 20 Drawing Sheets

OTHER PUBLICATIONS

Baim and Grossman,Cardiac Catheterization, Angiography, and Intervention, 5th ed., Chapter 27, Coronary Angioplasty, p. 537-547, 1996.

R. L. Webb, Principles of Enhanced Heat Transfer, p. 2, 1994.

Incropera, F.P. and DeWitt, D.P. Fundamentals of Heat and Mass Transfer, 4th ed., p. 599-607, 1996.

Merrill T.L. et al., Design of a cooling guide catheter for rapid heart cooling, ASME, J. Medical Devices, Sep. 2010—vol. 4, Issue 3, 035001 (8 pages) doi:10.1115/1.4002063.

Dae M. et al., Effect of endovascular cooling on myocardial temperature, infarct size, and cardiac output in human-sized pigs, American J. of Physiology, May 2002, vol. 282, No. 5, H1584-H1591.

\* cited by examiner

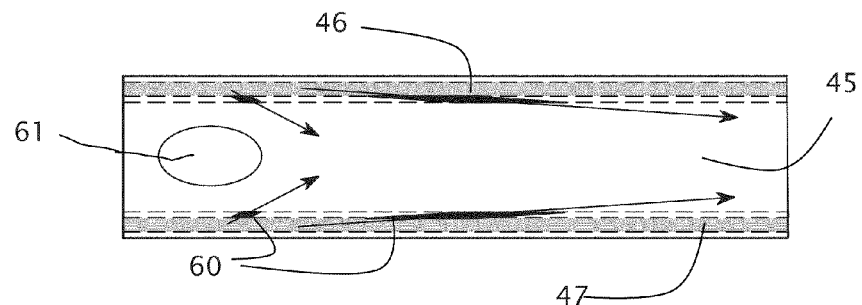
FIG. 28
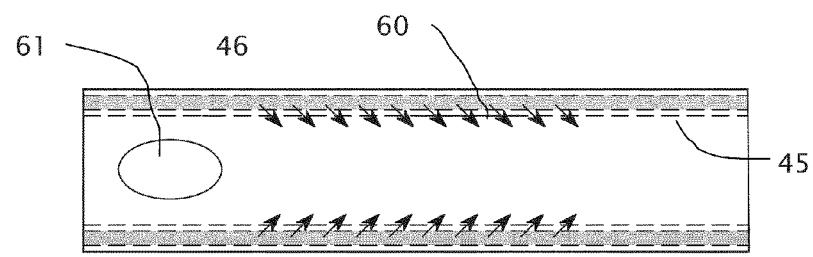
FIG. 29
FIG. 30
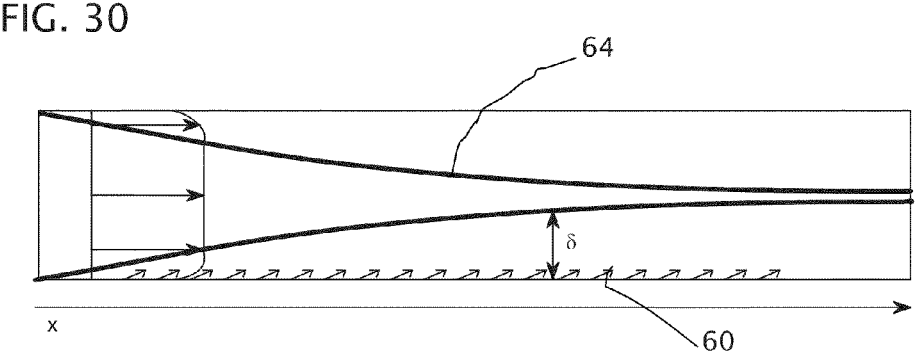

COOLING GUIDE CATHETER AND ASSOCIATED METHOD OF USE

CROSS-REFERENCE TO RELATED APPLICATIONS

The present application is a continuation-in-part of, and claims priority from, U.S. patent application Ser. No. 11/226,683 filed on Sep. 14, 2005 now abandoned, which is herein incorporated by reference. The '683 application in turn claims priority to U.S. Provisional Patent Application Ser. No. 60/610,333 filed on Sep. 16, 2004, and to U.S. Provisional Patent Application Ser. No. 60/650,297 filed on Jan. 26, 2005, both of which are herein incorporated by reference, and from which priority is claimed.

STATEMENT REGARDING FEDERALLY SPONSORED RESEARCH

The National Institute of Health provided support for the subject matter of this patent application under Grant #1 R43NS049933-01A1 (An Active Mixing Catheter For Selective Organ Cooling) and the United States government may have certain rights in this application.

BACKGROUND OF THE INVENTION

The present invention relates generally to a cooling catheter medical device such as may be used to guide interventional tools and to reduce reperfusion tissue injury, injury resulting after periods of ischemia, occurring naturally, through trauma, or from surgery, and further relates to the application of adjunctive therapies such as angioplasty and stent placement.

Heart disease is the leading cause of death in the United States. For heart attack, the primary treatment goal is rapid blood flow restoration to ischemic tissue. Despite the success of thrombolytic drugs and percutaneous coronary intervention (PCI) to reperfuse ischemic tissue, about 20% of all patients die within the first year following their first heart attack. Reperfusion is paradoxical, as reperfusion both saves tissue and kills tissue. Reperfusion injury is a critical barrier to improved patient outcomes, accounting for up to 50% of tissue injury. Reperfusion injury results in myocyte damage through myocardial stunning, microvascular and endothelial injury, and irreversible cell damage or necrosis.

A 2004 National Heart, Lung, and Blood Institute expert working group stated that current reperfusion therapies that included angioplasty, thrombolytics, and coronary bypass surgery have plateaued; new adjunctive therapies are needed to further improve patient outcomes. Quantitatively speaking: these strategies need to reduce infarct by 35% to reduce mortality rates in humans. In addition, the treatment method must not significantly alter current standards of care nor delay reperfusion.

Experimental evidence has shown that reductions in tissue temperature can reduce the effects of ischemia or inadequate blood flow and subsequent reperfusion. Hypothermia decreases tissue metabolism, microvascular obstruction and no reflow, oxygen free radical production, intercellular calcium overload. Hypothermia also inhibits platelet aggregation and preserves ATP and glycogen stores Despite hypothermia therapy's potential to attenuate myocardial necrosis, no cooling device has achieved approval for percutaneous coronary intervention because: 1) they complicate or impede the care path; and 2) they have not demonstrated significant clinical benefits. Reducing lingering heart damage following a heart attack due to reperfusion injury continues to be a large unmet need.

There are two broad categories of devices used to harness the therapeutic value of hypothermia: external systems and internal systems. Within these categories, subcategories of whole-body and regional cooling exist. Originally whole-body external systems consisted of immersion in cold water or forced cold air through blankets. An advanced external cooling system by U.S. Pat. No. 6,375,674 B1 to Carson, significantly improved cooling rates by adding a conductive adhesive layer between the skin and device, coolant pathways that provide relatively high speed coolant flows with resulting higher level convective heat transfer coefficients, and an insulated outer layer to the external walls to ensure heat addition from the ambient is minimal. While this approach is considered noninvasive, rapid temperature drop of organs at risk is not possible, rates of body temperature decrease are only about 3.2 degree Celsius per hour.

Invasive or vascular whole-body coolers have also been created, as shown in exemplary U.S. Pat. No. 6,096,068 to Dobak et al., U.S. Pat. No. 6,126,684 to Gobin et al., and U.S. Pat. No. 6,231,594 to Dae. In each of these cases, catheters are placed in a large vein called the vena cava. Passive heat transfer enhancement techniques are used to accelerate whole body cooling. These techniques consist of either increasing surface area, increasing fluid mixing or turbulence, or increasing both surface area and turbulence simultaneously. Again, these approaches do not allow for rapid organ cooling; whole-body cooling rates range from 2 to 5 degrees Celsius per hour. These passively enhanced techniques also consume fluid kinetic energy, reducing blood flow and potentially re-creating ischemic conditions, making them less suited for low flow, small diameter applications as found in organ arteries. The vena cava has an inner diameter of approximately 22 mm carrying 5000 ml/min of blood flow; in comparison a left coronary artery has an inner diameter of approximately 4 mm carrying 125 ml/min of blood flow. Alternative patents, such as U.S. Pat. No. 7,211,066 to Merrill describe active enhancement methods that avoid kinetic energy dissipation and are more suited for organ arteries such as the left coronary artery and a carotid artery.

Current research indicates that more rapid cooling is needed to reduce the final extent of organ damage following ischemic events such as stroke and heart attack and improve patient outcomes. A cooling rate of 4 degrees Celsius in five minutes (48 degrees Celsius per hour) has been suggested. This represents an order of magnitude increase in cooling capacity compared to whole-body cooling devices. In addition whole-body cooling has additional limitations and drawbacks related to its inherent unselective nature. Research has shown that systemic or whole body cooling may lead to cardiovascular irregularities such as reduced cardiac output and ventricular fibrillation, an increased risk of infection, and blood chemistry alterations.

Few concepts have attempted local, organ-specific cooling. Local cooling approaches have been limited by the technological challenges related to developing sufficiently small heat exchangers for small arterial vessels. These vessel inner diameters are typically less than 6 mm, whereas larger systemic vessels are 20 mm or larger. The key advantage to localized or organ level cooling is the reduced thermal inertia, since the cooling capacity required is directly proportional to the product of the mass and specific heat. Cooling 100 grams of heart tissue (approximately one-third of the heart) vs. an entire 70,000 gram patient takes significantly less cooling capacity to reach equivalent reduced temperatures. In addition the rate of cooling is substantially greater with localized organ specific cooling.

One ideal application for organ-specific cooling is emergency angioplasty. When patients suffer a heart attack there are three broad categories of care: thrombolytics—breaking done a blood vessel blockage with chemicals, coronary artery bypass surgery—creating a bypass around a vessel blockage, and emergency angioplasty. The emergency angioplasty care path has been well-established since the 1980's. In this case the reperfusion event, when the blood rate resumes to levels above critical ischemic thresholds, is controlled by the physician and medical staff. Therapeutic hypothermia applied during emergency angioplasty is considered an adjunctive therapy.

Angioplasty involves recanalization or reopening of block organ arteries with dilation or balloon catheters. Prior to recanalization there is a stenosis or blockage preventing adequate blood to the organ of interest, creating an ischemic event that eventually leads to a reperfusion event if the stenosis can be removed. As each minute passes with flow completely halted or below an ischemic threshold of 0.12 to 0.24 ml/min/g of tissue, more organ tissue is lost. Organ tissue closest to the blockage, called the ischemic core, is most vulnerable to irreversible damage. The region between healthy perfused tissue and the ischemic core is called the pneumbra. This is the region that has the potential of being saved with effective adjunctive therapies.

To understand how therapeutic hypothermia may be an effective adjunctive therapy an overview of the angioplasty care path is needed. Critical medical devices used during this procedure will be discussed immediately in the following paragraphs. Coronary angioplasty with a single stenosis begins with the insertion of an introducer or insertion sheath used to enable access to the patient's vascular system. Once the patient activating clotting time (ACT) has been altered by heparin or similar agent to avoid thrombus formation on the interventional tools, a guide catheter is threaded into the insertion sheath towards the coronary artery of interest. Once at the ostium or intersection of the aorta and the coronary artery, the distal tip (the end of the catheter) engages the coronary artery and a baseline angiogram is conducted. A baseline angiogram uses contrast agent (a fluid that can be seen through fluoroscopy) to establish the precise location of the stenosis. After the location of the stenosis has been identified, a guide wire is steered across the stenosis. With the guide wire fixed in place a dilation or balloon catheter is threaded along the guide wire and towards the stenosis. Once the dilation catheter balloon is positioned directly inside the stenosis, the balloon is inflated progressively, compressing the lesion or blockage material radially outward. In addition to balloon dilation today's interventional tools also include stents that are metal supports to avoid restenosis and thrombectomy devices that mechanically remove lesion material. Once acceptable perfusion and or reperfusion are established and verified through angiograms, the dilation catheter, the guide wire, and the guide catheter are removed. Finally the insertion sheath is removed and the patient is moved to a recovery area where the penetration wound heals and the patient is monitored.

An effective therapeutic hypothermia device that is organ-specific needs to integrate with the emergency angioplasty care path, taking into account the physical features and operational aspects of the medical devices or components used.

The insertion sheath provides an entry pathway into the vascular system, connecting the outside world to the vascular world. It is a tapered tube with a hemostat, a one-way valve to prevent blood loss. A side port allows secondary blood access to monitor blood characteristics during procedures and the tapering minimizes the wound size resulting from angioplasty.

Guide catheters are threaded through the insertion sheath and their simple exterior hides their complexity. Guide catheters serve four functions: 1) they are a conduit for device and wire transport, 2) they support device advancement (in some cases lesions are not easily traversed by dilation catheters), 3) they are conduits for contrast injection, and 4) they provide a means for blood pressure measurement. To perform these functions they must have these physical features: 1) a rear hub that allows for easy and secure connections with interventional devices such as guide wires, thrombectomy devices, dilation catheters, and manifolds for pressure measurement and contrast delivery; 2) a distal tip shape that integrates well with patient anatomy so that the catheter and artery are coaxial; 3) a distal tip material that is radiopaque so that it can be visualized with fluoroscopy; 4) a distal tip that will not damage vessels, also called atraumatic; 5) a shaft that allows for torque control to guide the distal tip correctly; 6) a shaft that is kink resistant; 7) a shaft with an inner diameter sufficiently large or compatible to pass interventional tools (dilation, stent, thrombectomy, etc.); 8) a shaft that is sufficient rigid or stiff to provide support for interventional device placement and will not dampen pressure signals; and 9) a shaft that is lubricious, meaning a shaft material that allows interventional tools to pass easily.

Medtronic, a leading manufacturing of guide catheters such as the Launcher™ guide catheter, lists 28 distal shapes or curves for catheter shafts available to physicians. Proper placement of the guide catheter will largely depend on these distal shapes and active rotation of the catheter by the physician. The contralateral wall, the wall opposing the ostium, is typically used to support or buttress final placement. Proper engagement of the ostium requires coaxial alignment and some annular space between the catheter outer wall and the inner wall of the ostium, avoiding arterial flow occlusion. To meet the shaft functionality the walls of a guide catheter are usually a composite of polymers and metal, as shown in U.S. Pat. No. 5,531,721 to Pepin et al. The outer wall is designed to be smooth and hemocompatible, a stainless steel braid provides the mechanical properties, and finally an inner low coefficient of friction polymer is used as a inner liner or coating.

Guide wires range in size from 0.010 to 0.038 inches. To ensure ease of placement across lesions a variety of stiffness levels are used at the distal tip. Shaping of the distal tip is also possible. Surface coatings, such as hydrophilic coatings enhance maneuverability. Guide wire torque devices, located outside the guide catheter hub, are attached to the proximal end and radiopaque materials at the distal end help ensure precise placement under fluoroscopy.

Dilation catheters provide the radial force to reduce the amount of cross sectional area blockage occurring at a lesion. Thanks to improved balloon design, balloon materials (such as polyethylene (PE) and polyethylene terphalate (PET)), and balloon wrapping techniques improved patient outcomes have been achieved. Typical catheters like the Medtronic Sprinter® OTW have crossing profiles that are 0.021-0.024 inches (0.53 mm to 0.61 mm), where the crossing profiles is the diameter of the balloon in a fully wrapped and collapsed position. Lesion entry profiles, the diameter at the distil tip of the dilation catheter, are 0.016 inches (0.41 mm). Catheterization guidelines recommend that the crossing profile be at most one-half the inner lumen of the guide catheter to ensure low force passage to the artery of interest. At these preinflation profiles, fully inflate balloon diameters range from 1.5 to 4.0 mm at pressures ranging from 4 to 18 atmospheres. In addition to these geometric characteristics today's dilation catheters also use shafts that are designed for trackability, the ability to follow along tortuous paths, and pushability, the ability to force through a lesion provided it has sufficient stiffness. Finally, surface coatings are used to improve surface lubricity so that frictional resistance is minimized.

While rapid localized organ cooling may potentially reduce damage from ischemia few references have described a way to integrate into the emergency angioplasty care path. Often, the physical features of conventional catheter medical devices do not allow for integration with emergency angioplasty interventional tools, namely from a flexibility and size perspective. In addition because they rely on passive heat transfer enhancement methods blood flow resistance to increases, reducing perfusion to already damaged organs recovering from ischemic events. This blood resistance comes as a direct of result of the design features: 1) an enhanced surface area (more area for flow-resistive shear stress to act upon) 2) a cooling surface geometry that causes increased fluid mixing (causing viscous dissipation of kinetic energy), and 3) a reliance on the pumping power of the heart to push fluid over the heat exchanger surfaces (energy from the heart provides the energy require for mixing).

U.S. Pat. No. 6,645,234 to Evans et al. describes a cardiovascular guiding catheter with heat exchange properties. In this patent there are five lumens and inflatable external balloons used to exchange heat away from systemic blood flow in the descending aorta, the major artery leaving the heat. This design provides a means for systemic or whole-body cooling while also acting as a guide catheter. Whole-body cooling, however, does not address organ-specific reperfusion injury resulting after an ischemic event, the clinical problem that this patent addresses As described earlier, there are several existing external and internal whole-body cooling devices that produce cooling rates ranging from 2-5 degrees Celsius per hour. In addition to not providing a means for rapid organ-specific cooling, the '234 Evans et al. device has several disadvantages from a guide catheter perspective. First, braiding does not extend to the distal tip in this patent, removing a critical physical feature necessary to provide support of dilation catheter placement and kink resistances. Second, inflation and deflation of the external balloons make device removal from the patient more difficult and will likely require a large insertion sheath than is typically needed. Increased insertion sheath sizes lead to longer healing times and increased complications, the motivation in the commercial market for continued reduction in guide catheter sizes since the angioplasty procedure was introduced. Third, the external balloons will naturally limit the maneuverability of the distal tip as the walls of the aorta are used to buttress or support proper guide catheter placement. Fourth, the lubriciousness of the inner and outer surfaces is unclear. Typically Teflon is used to reduce the friction resistance in guide catheters. External balloons add significantly more area over which friction forces act. Finally, these external balloons create significant blood stagnation zones as the catheter contacts the aorta in comparison to standard guide catheters. Based on cardiovascular support design fundamentals, these zones are considered likely locations for thrombus or clot generation.

U.S. Pat. No. 6,033,383 to Ginsburg, U.S. Pat. No. 5,180,364 to Ginsburg, and U.S. Patent Application Publication No. 2001/0005791 A1 to Ginsburg each describe temperature regulating devices for controlling liquid medium temperatures inside a patient. The Ginsburg devices have several disadvantages against application to reduce tissue damage arising from reperfusion injury following emergency angioplasty procedures. To ensure adequate cooled blood is delivered safely and easily during an emergency angioplasty procedure, described above, many of physical features and functions of existing angioplasty equipment are needed. The design intent of the '383 Ginsburg device is clearly to transfer fluids, not interventional tools associated emergency angioplasty. As a result, embodiments do not address torque control, kink resistance, and support characteristics through catheter shaft design. Regarding the inner most lumen, lubriciousness or friction-resistance is not addressed. Internal flaps represent an order of magnitude increase in surface roughness relative to the roughness of typical coatings and liners used to deliver interventional tools. Teflon, the standard coating, has a roughness around $6e^{-5}$ inches or $1.52e^{-3}$ millimeters.

The flaps shown in the Ginsburg devices could not operate as described. First to properly seal the inner, a rectangular leaflet or flap would need to bend or curve along the curvature of the inner diameter of the inner lumen. Second, even if the flap was bent to meet the radius of curvature of the inner diameter of the circular device, flap deflection would be inhibited or perhaps prohibited completely because of the orthogonal curvature relative to the desired axis of rotation. No existing catheters implement this valve design. Embodiments do not describe the distal tip requirements necessary for effective, safe, and easy placement for rapid organ-specific cooling as in emergency angioplasty. For example to engage the ostium of the heart these embodiments do not describe the necessary shape or shaft support necessary to locate and deliver interventional tools. In fact, if the double concentric embodiment is shaped in standard shapes such as a hockey stick or Judkins Left or Right, liquid pathways used to transfer heat would clearly pinch onto one another, shrinking the internal pathways. Considering the small radius of curvature required for standard guiding catheter shapes, Judkins Left or Right, embodiments using internal liquid flow would likely kink. Because liquid pressure drop is inversely dependent on the hydraulic diameter raised to fourth power or higher, depending on the flow regime (laminar or turbulent), small reductions in liquid pathway size make a substantial increases in fluid pumping pressure requirements. For non-circular pathways the hydraulic diameter is defined as four times the cross-sectional area divided by the wetted perimeter (the perimeter where liquid is touching solid surface).

Regarding heat transfer performance, the liquid flow double concentric embodiment of the device shown in the '383 Ginsburg patent as the preferred embodiment, has several disadvantages. First, the double concentric design limits fluid pumping rates because the hydraulic diameters are inherently reduced due to the concentric nature of the design. The hydraulic diameter in an annulus is the diameter difference between the two enclosing tubes. At small hydraulic diameters high pressures are needed to push liquid to accomplish heat transfer. Pressures that have been used to safely operate cooling devices are in the range of seven atmospheres. At this maximum pressure range the flow will be determined by the fluid viscosity, the path length of the fluid, and the hydraulic diameter. While pressure drop is linearly dependent upon viscosity and path length, it is inversely dependent to the fourth power or higher on the hydraulic diameter. In this case, two design features of the double concentric embodiment as shown in the '383 Ginsburg patent design significantly impede liquid flow: a) the reduced hydraulic diameters; and b) the path length which is double the overall length of catheter. Impeding liquid flow reduces heat transfer coefficients and creates a longer residence time for the liquid to travel the path length. Increased residence times lead to larger liquid temperature changes; the heat transfer liquid in the annulus essentially warms or cools to the surrounding temperatures more readily. Once the liquid temperature change is sufficiently large, the temperature difference between the heat exchange fluid temperature in the annulus and the injected fluid temperature in the inner lumen is eliminated and the device no longer acts as heat exchanger.

Second, the described liquid pathways are parallel flow, in other words the injected liquid is flowing parallel in the same direction as the nearest heat exchange fluid. This arrangement, based on established heat transfer references, inherently limits the maximum possible heat transfer possible substantially, typically 20% to 60% less than counter current flow arrangements depending upon the setup of the heat exchanger. In this case, based on thermodynamics laws, the exiting warm liquid can never have a temperature below the temperature of the cool liquid. In addition, the double concentric design of the device of the '383 Ginsburg patent inherently limits the overall heat exchange process because the returning flow in the outer annulus is exchanging heat with inner annulus flow. In the case of cooling the injected the fluid, the outer annulus flow acts to warm the inner annulus flow since the inner annulus flow has removed heat from the warmer injected liquid flow.

Third, blood flow entry into the inner most or central lumen via the depicted valves of the '383 Ginsburg references is inherently limited. If the flaps as described earlier could be hinged internally, deflected in the described manner, and did not impede placement or removal of interventional tools that include but are not limited to guide wires, dilation catheters, and thrombectomy devices, creating actual blood flow requires a sufficient hydrostatic pressure difference between the external blood flow outside the catheter at the holes and the external blood flow outside the catheter at the distal tip. In the embodiments described in the Ginsburg references, this pressure difference will depend on five factors: 1) the side holes or orifice diameter; 2) the orifice roughness; 3) the stiffness of the flaps; 4) the opening created at the flap; and 5) the pressure drop along the path length along the central lumen. These factors hinder the ability of blood to flow at a fixed pressure difference, an undesirable condition for arterial blood flow to already ischemicly damaged organs.

Fourth, the arrangement and orientation of the valves in the Ginsburg devices, along the shaft perimeter of the patent prevent or at least substantially hinder coolant flow along the length of the catheter. While the patent claims a section distal to the valves is a "temperature altering region", a means to accomplish this unclear.

In summary, the previously described patents have one or more of these disadvantages:

The designs do not take into account the physical characteristics of existing guide catheters that are based on thirty years of refinement: support for dilation catheter advancement, shape to allow coaxial placement inside arteries for organs at risk, mechanical structure to avoid kinks and ensure placement control, and distal tips that are atraumatic.

The designs are focused on large diameter vessel blood cooling or whole-body cooling, not small artery or organ-specific cooling where flow resistance can easily be increased leading to additional ischemic injury The designs do not apply heat exchanger best practices well established for decades such as maximizing hydraulic diameters to reduce coolant pressure drop and using counter current flow configurations that maximize the potential heat transfer.

Accordingly, it would be advantageous to develop interventional catheters which accommodate the physical characteristics of existing guide catheters, including support for dilation catheter advancement, which are shaped to allow coaxial placement inside arteries for organs at risk, which have mechanical structure capable of avoiding kinks and ensuring placement control, and which have distal tips that are atraumatic.

It would be further advantageous to develop interventional catheters which are capable of small artery or organ-specific cooling without increasing ischemic injury due to flow resistances.

BRIEF SUMMARY OF THE INVENTION

Briefly stated, the present disclosure provides an cooling catheter in which blood in contact with cold surfaces is cooled and delivered to an injured organ to minimize reperfusion injury.

In one embodiment the cooling catheter incorporates heat exchange surfaces, two non-circular lumens for coolant circulation, a central lumen for blood flow and interventional device passage, and a rear external hub to connect the device to outside controls and to engage interventional tools. The cooling catheter is additionally coupled to a cooling console to carefully circulate blood inside a circular lumen used for blood delivery and interventional device delivery, allowing continuous blood delivery and cooling while typical interventional tools are used.

In a further embodiment, the cooling catheter is configured to utilize natural pressure differences between a patient's aorta and an injured organ to motivate blood flow through the cooling catheter. Blood cooling occurs as exiting cold blood mixes with normothermic blood and is delivered to injured organs.

In a further embodiment, the cooling catheter is incorporated into a hybrid surface-infusion cooling device. Coolant infusion from coolant lumens within the catheter shaft into a central blood conveyance lumen enhances cooling catheter blood flow performance in two ways: 1) by reducing near-wall viscosity, reducing flow-limiting wall drag and 2) exchanging momentum with the blood flowing within the blood conveyance lumen.

In one embodiment a catheter apparatus provides a delivery system for standard intervention devices typically used during emergency angioplasty and to provide rapid localized cooling to organs at risk of ischemic and reperfusion injury. The catheter maintains the characteristics of existing guide catheters, leaving the current care path for emergency angioplasty unaltered, while also providing a means to cool organs at rates of 4 degree Celsius per 5 minutes or greater.

Besides the advantages of maintaining current guide catheter delivery features with cooling capabilities, embodiments of the present disclosure provide: (a) a catheter that is structurally designed to be steered, without kinking or torsional energy storage, to the organ at risk of ischemic and reperfusion injury; (b) a catheter that is shaped like a standard guide catheters to enable coaxial engagement with target vessels; (c) a catheter that is able to engage the target vessel easily and safely using radiopaque and atraumatic features; (d) a catheter that has sufficient internal lumen size and surface that allows low resistance insertion of a variety of interventional tools such as guidewires, dilation catheters with stents, diagnostic catheters, and thrombectomy catheters while continuously delivering cooled blood to an injured organ; (e) a catheter that cools blood to at least 28 degrees Celsius at flow rates of 30-100 ml/min; (f) a catheter that can provide the above mentioned cooling capability without external blood pumps; and (g) a catheter that can carefully control the organ-specific cooling process through using temperature, pressure, and flow sensors.

The foregoing features, and advantages set forth in the present disclosure as well as presently preferred embodiments will become more apparent from the reading of the following description in connection with the accompanying drawings.

BRIEF DESCRIPTION OF THE SEVERAL VIEWS OF THE DRAWINGS

In the accompanying drawings which form part of the specification:

FIG. 28 is a top view schematic of blood flow into the cooling catheter accompanied by infusion of coolant through infusion holes as the blood travels towards the distal tip along the inner lumen;

FIG. 29 is a view similar to FIG. 28, illustrating additional infusion entry holes;

FIG. 30 shows a cross section schematic inside the cooling catheter of FIG. 29, illustrating how a boundary layer develops as blood enters the catheter along with the coolant infusion that takes place inside the boundary layer;

Corresponding reference numerals indicate corresponding parts throughout the several figures of the drawings. It is to be understood that the drawings are for illustrating the concepts set forth in the present disclosure and are not to scale.

Figure 1:
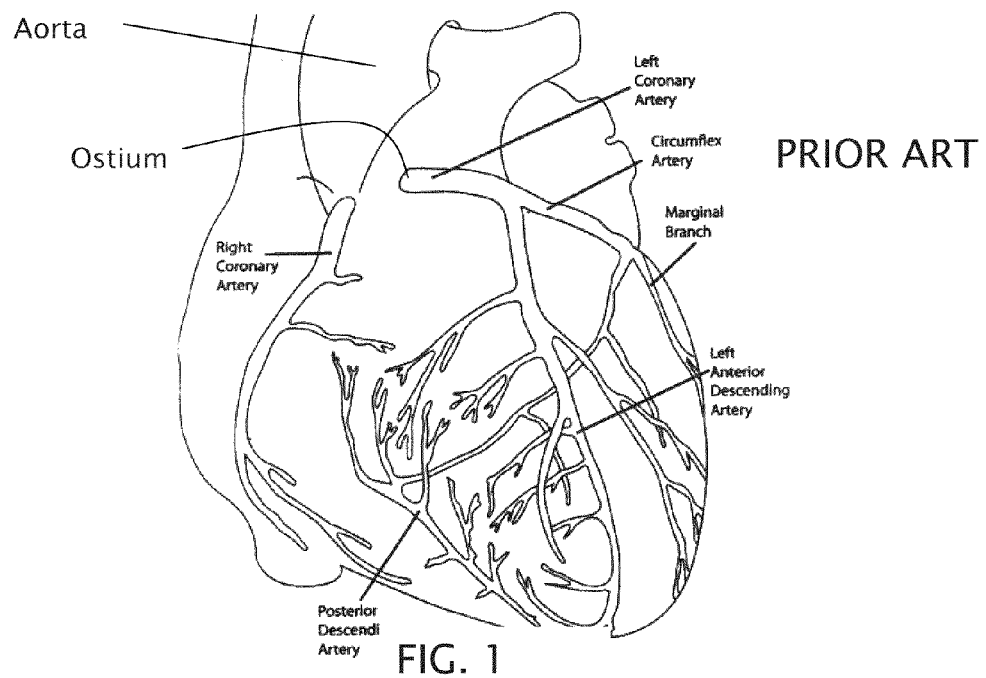
FIG. 1 is a prior art perspective view of the arterial pathways of a human heart.

Before any embodiments of the invention are explained in detail, it is to be understood that the invention is not limited in its application to the details of construction and the arrangement of components set forth in the following description or illustrated in the drawings.

DETAILED DESCRIPTION

The following detailed description illustrates the invention by way of example and not by way of limitation. The description enables one skilled in the art to make and use the present disclosure, and describes several embodiments, adaptations, variations, alternatives, and uses of the present disclosure, including what is presently believed to be the best mode of carrying out the present disclosure.

Figure 2:
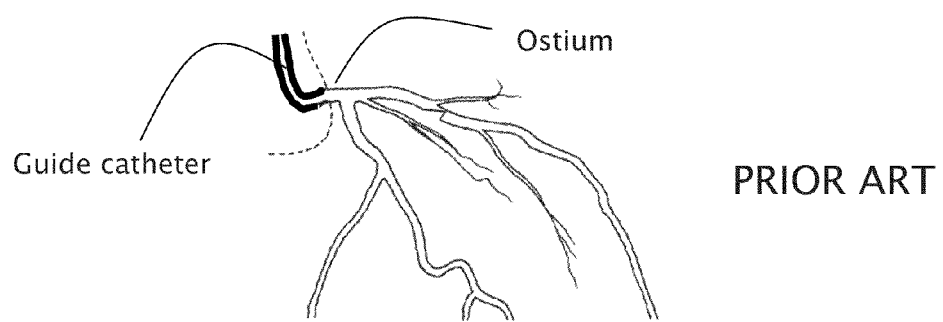
FIG. 2 is a prior art illustration of placement of a guide catheter in a human ostium.
Figure 3:
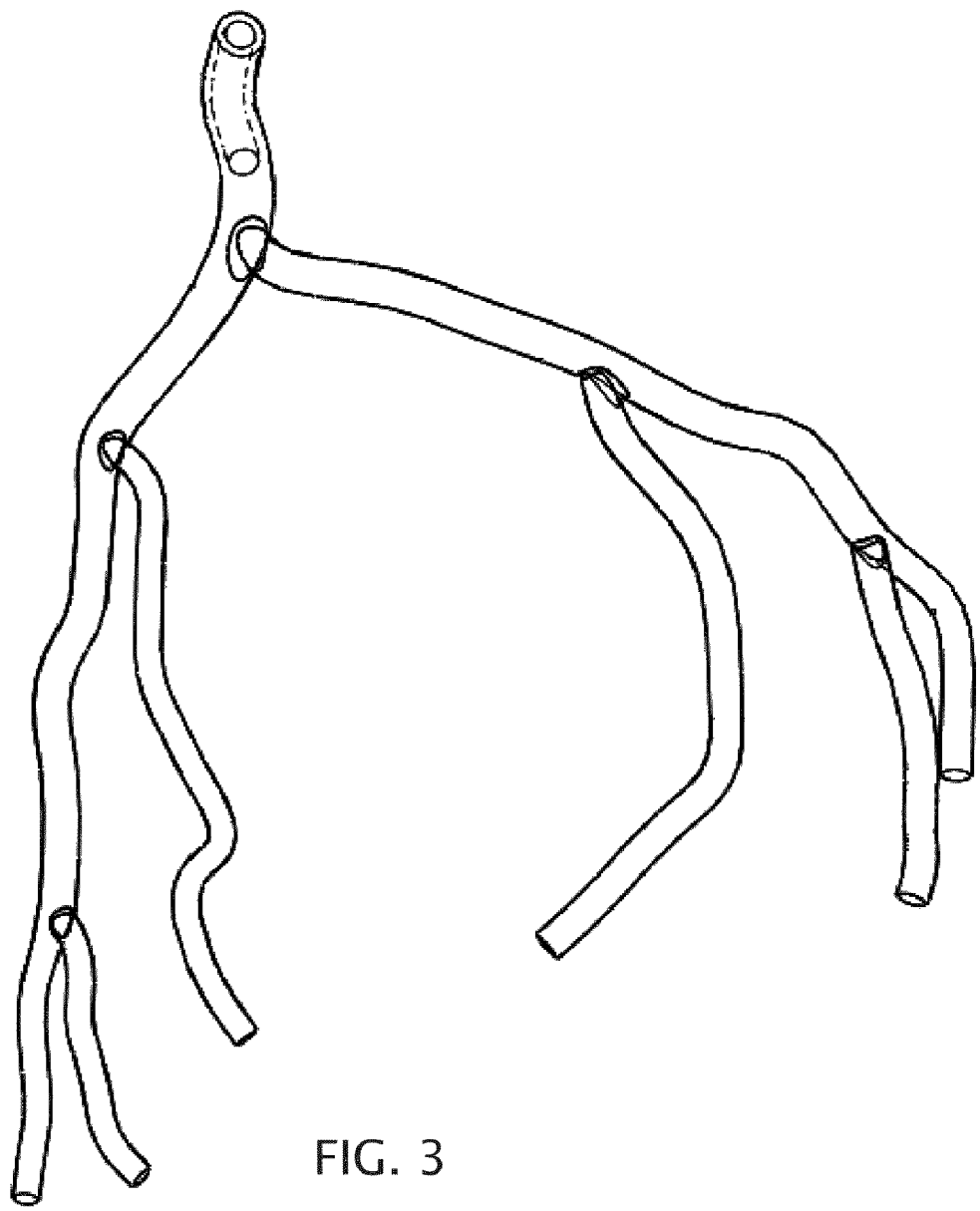
FIG. 3 is a three-dimensional view of FIG. 2.

Turning to the figures, is can be seen that FIG. 1 through FIG. 3 shows the physiological landscape where embodiments of the present invention can be used. FIG. 1 shows a drawing of the major arteries of the heart. The coronary arteries (as seen in FIGS. 1-3) have proximal inner diameters ranging from 1.5 to 4.0 mm and length ranging from 2-4 cm. These arteries taper down in the direction of blood flow. FIGS. 2 and 3 show proximal and full engagement of a conventional guide catheter in the left main coronary artery, respectively. The large arteries carry out bulk transport of blood with minimal oxygen exchange. The majority of oxygen exchange and heat exchange take place at the capillary level where vessel inner diameters are several microns instead of several millimeters.

Figure 4:
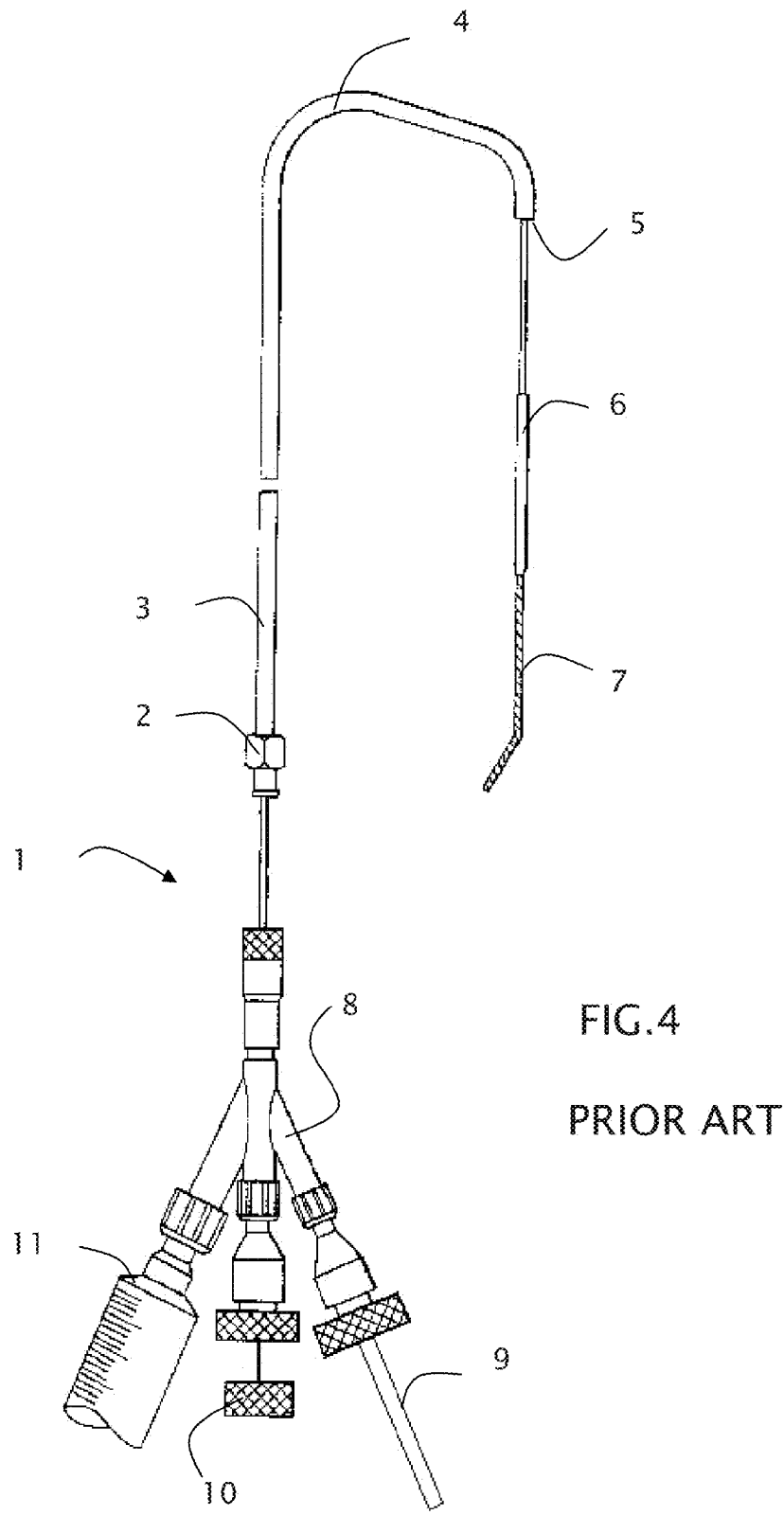
FIG. 4 is an illustration of a prior art angioplasty catheter assembly.

To appreciate the present medical device landscape FIG. 4 shows a standard angioplasty catheter assembly 1 with a guide catheter, such as placed into an artery as seen in FIGS. 2-3, which acts a conduit from the outside the patient to the heart. The guide catheter is made up of three distinct parts, the proximal hub 2, the shaft 3, and the distal tip 5. Along the shaft 3, shaped sections 4 are physician selected for easy placement in the patient. A balloon or dilation catheter 6 may be passed through the shaft 3 and used to removed artery blockages or stenoses by flattening atheroma, the material that builds along the interior walls in artery disease. A guide wire 7 is used to carefully and precisely locate the dilation catheter during placement. At the proximal hub 8 of the angioplasty catheter assembly 1 there are three components, the proximal hub of the dilatation catheter 9, a torque guide 10 for the guide wire, and a contrast syringe 11 for conducting angiography, a process used to visualize stenoses and proper blood flow using fluoroscopy.

Figure 5:
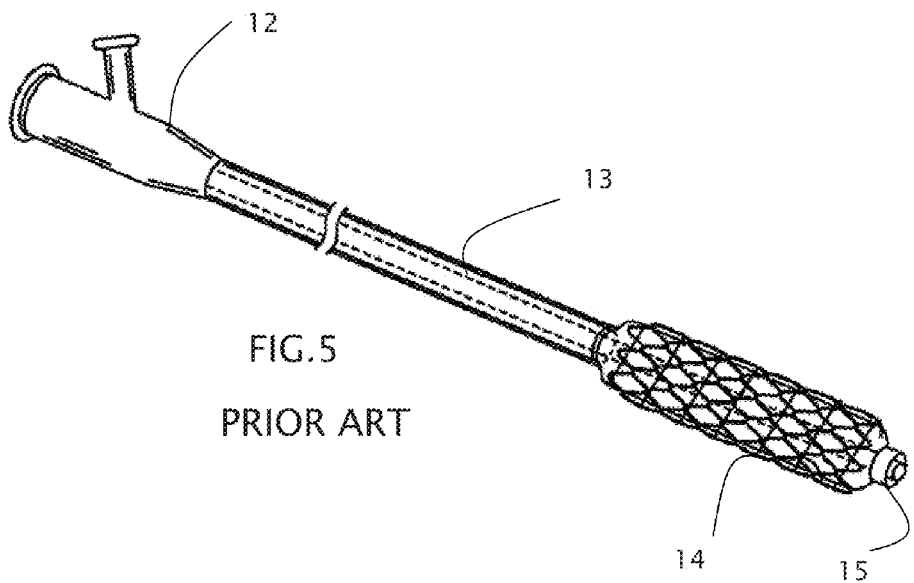
FIG. 5 is a perspective view of a prior art catheter assembly used to deliver an interventional device (stent) used to maintain a pathway for blood flow

In addition to angioplasty catheter assemblies FIG. 5 shows an exemplary conventional catheter assembly used to deliver a stent 14, an interventional device used to maintain a pathway for blood flow after an interventional procedure. The guide catheter 12 encloses a dilation catheter 13 that has a stent 14 expanded by a balloon 15. The stent 14 is essentially a cylindrical cage that is expanded against the inner lumen of a diseased vessel.

Figure 6:
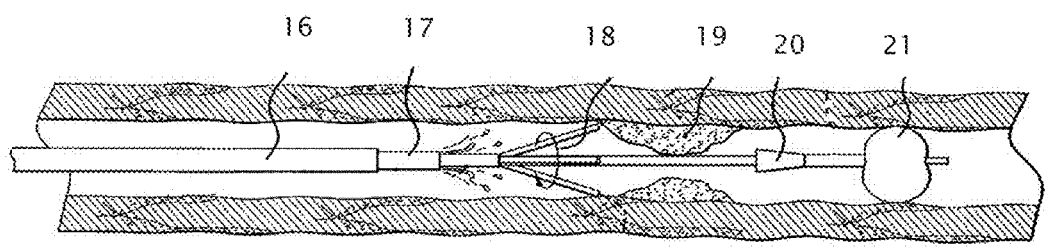
FIG. 6 is an illustration of a prior art thrombectomy catheter in use removing hard or calcified plaque inside a diseased artery.

FIG. 6 shows yet another interventional device called thrombectomy catheter for removing hard or calcified plaque inside a diseased artery. A large telescoping shaft 16 and small telescoping shaft 17 transports a spinning cutting member 18 into position so that it can cut into accumulated plaque 19 within the artery. A fusiform member 20 and balloon 21 are used to limit thrombus particles from being carried downstream towards capillary vessels.

Figure 7:
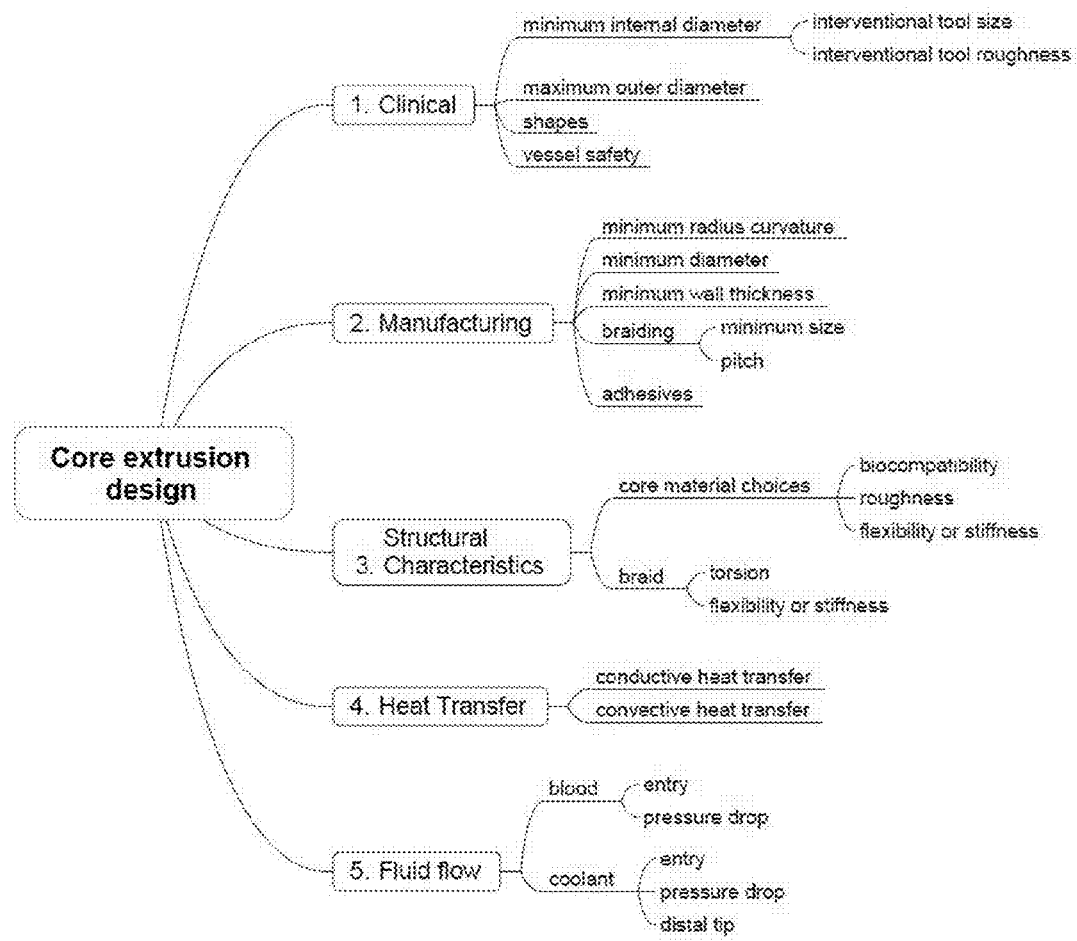
FIG. 7 is a diagrammatic representation of design factors for the cooling catheter of the present disclosure.

With the physiological and medical device landscaped described, FIG. 7 identifies various design constraints that are considered when forming a cooling catheter of the present disclosure. These fundamental constraints help define the maximum and minimum geometries and material selections based on physics, established practices, and commercial norms.

In terms of clinical constraints, the minimum inner diameter of the blood conveyance lumen through the catheter shaft is based on the typical outer diameters of interventional devices, including but not limited to, the devices described above. The maximum outer diameter of the catheter shaft is based on physician preferred sizes, largely driven by concerns related to wound healing after introducer sheath removal. Physiological differences dictate the need for a variety of shapes for proper placement. Concern about vessel damage either through scraping or puncture dictate that exterior surfaces be atraumatic.

Regardless of what physicians want or what may or may not be safe, there are limits from a practical manufacturing perspective in terms of feasibility and cost. Since most catheters are made from plastic extrusions, the extrusion process is limited to certain minimum diameters, radii of curvature, and wall thicknesses. Reinforcing braids woven into the peripheral walls of the cooling catheter shaft are similarly limited, and adhesives have bond strengths that vary with materials chosen.

Once the clinical and manufacturing constraints are established, the physical constrains are considered. These include structural characteristics, heat transfer and fluid flow characteristics. These physical characteristics refine the gross features established by the clinical and manufacturing constraints. For example, tissue cooling rates establish device heat transfer requirements. Those heat transfer requirements define the coolant flow requirements. Those coolant flow requirements determine the pressures or internal stresses that devices experience. In the end the goal of maximizing heat transfer is counter balanced with the need ensure structural integrity as high pressure is circulated through an embodiment.

Figure 8:
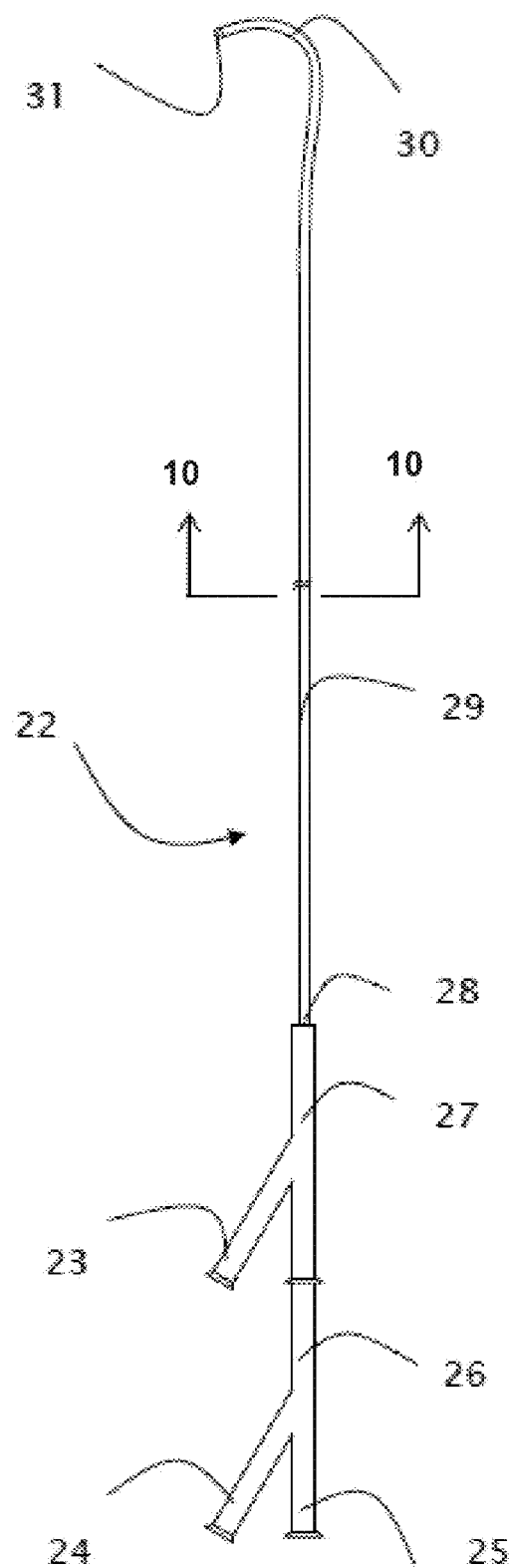
FIG. 8 is an illustration of a cooling catheter assembly of the present disclosure.

An overall view of the preferred embodiment of the present disclosure is illustrated in FIG. 8. The complete catheter assembly 22 is made from four sections, proximal hub 26, proximal hub 27, a shaft 29, and a distal end, 30. The most proximal hub 26 allows interventional pathway of tools previously described through a rear access port 25 while also providing cooling inlet access through a second port 24. The next proximal hub 27 provides an outlet for coolant at a separate port 23. To reduce hub-shaft stress, a strain relief 28 may be utilized used to avoid kinking between the hubs and the shaft 29. Similar to existing guide catheters the distal shaft 30 may be provided with curved shapes such as Judkins Left or Judkins Right to facilitate placement near or into the ostiums of the patient. The distal end 30 terminates in a tip 31, fitted with a flexible polymer such as silicone, to avoid vessel damage during placement.

Figure 9:
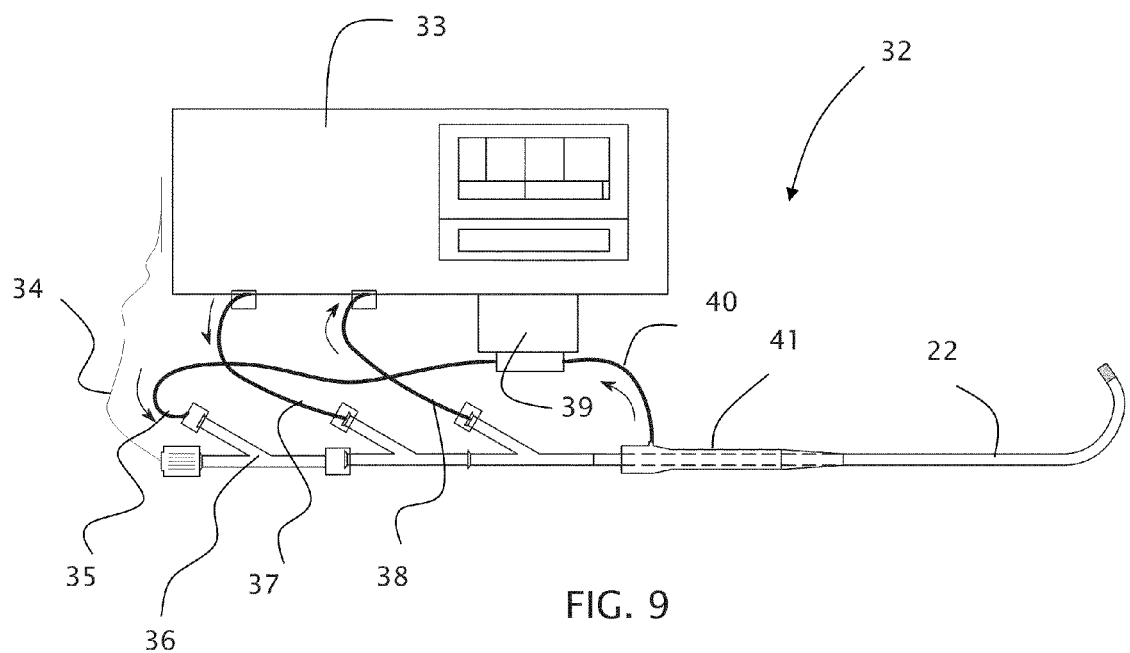
FIG. 9 is an illustration of a cooling system for use with the cooling catheter of FIG. 8.

Rapid localized organ tissue cooling is achieved when the catheter assembly 22 is used with a cooling console 33 to create a cooling system 32 as shown in FIG. 9. Working together, this assembly pulls blood from a patient and carefully pumps it in an open circuit, controlling the pressure, temperature, and flow rate of blood delivered to an injured organ. It has the capability to perform this activity during typical interventional procedures such as angioplasty, providing continuous cold blood flow to injured organs throughout the interventional procedure.

The cooling console 33 in FIG. 9 controls and monitors coolant flow rate, blood flow rate, and blood pressure levels, as well as the exiting blood temperature and coolant inlet and outlet temperatures. To carefully monitor blood delivery a thermocouple 34 is used to measure temperature of blood exiting the distal tip 31 of the catheter 22. Following the blood flow path throughout the cooling system 32, blood is first pulled from a main vessel in which the catheter 22 is place, through an introducer sheath 41, into blood tubing 40, and then circulated through a peristaltic pump 39. The blood is then pumped inside biocompatible tubing 35 to a rear connector 36 that provides access to the interventional port 25, as shown in FIG. 8. Coolant inlet port 24 is connected to the coolant inlet tubing 37, while the coolant exit port is connected to the coolant exit tubing 38. To ensure a continuous delivery of cooled blood, warmed coolant then enters the cooling console 33 to be re-cooled internally. This re-cooling ensures the that inlet coolant temperatures in the coolant inlet tubing 37 are held constant and therefore ensuring a constant temperature gradient between normothermic blood and the walls of the cooled catheter 22.

Figure 10:
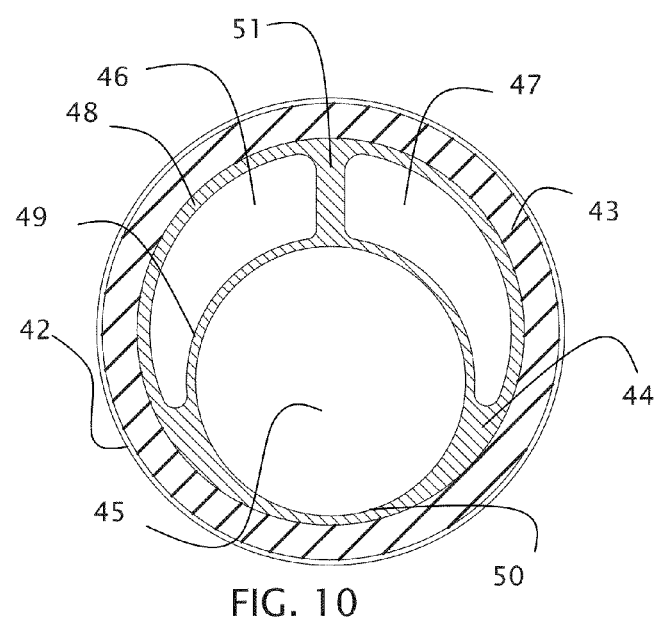
FIG. 10 is a cross-sectional view of the cooling catheter of FIG. 8.

To provide passages for interventional tools, blood flow, and coolant flow, the catheter shaft 29 of the catheter assembly 22 has a cross-section or profile as shown in FIG. 10. The outside wall 42 is composed of a polymer, with wall thickness of approximately 0.004±0.001 inches (0.1±0.025 mm). These polymers may include polyethylene, polyurethane, and polyether blocked amide such as Pebax™. Embedded in this polymer is a reinforcing braiding 43. The braiding 43 is made of stainless steel or a mono-filament fiber. Typical braid thicknesses are around 0.025-0.075 mm. The composite outer wall 42 and braiding 43 has a combined thickness of 0.18 mm to 0.35 mm. This outer wall makeup significantly improves catheter flexural stiffness and longitudinal stiffness, allowing physicians to more easily place the catheter inside the patient. The composite outer wall 42 and reinforcing braiding 43 also buttresses the insertion of dilation catheters as these catheters are placed into the lesions of diseased small arteries.

A feature seen in the preferred embodiment is the inner core 44, which can be best described as having the configuration of a bisected eccentric annulus. The inner core 44 is a multi-lumen extrusion made of a lubricious material such as polytetrafluoroethylene (PTFE or Teflon™). The inner core 44 provides pathways for both bi-directional coolant flow and blood flow and directly results from the design constraints described earlier in FIG. 7. For example, the minimum diameter, the minimum radius of curvature, and the minimum wall thickness are all determined by practical manufacturing constraints and further influenced by critical heat transfer, fluid flow, and structural constraints.

Figure 16:
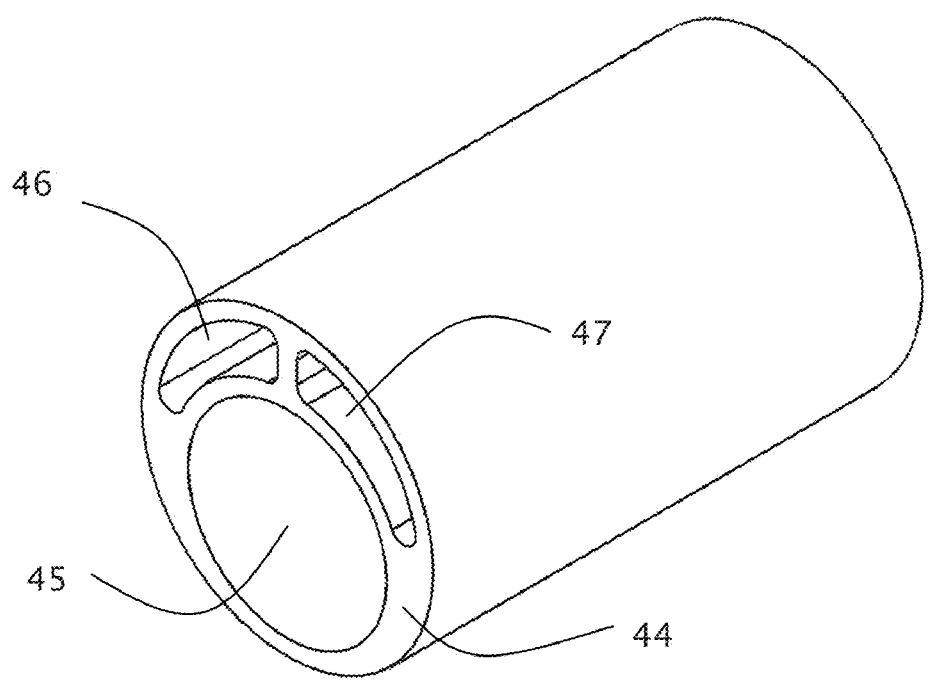
FIG. 16 is an isometric view of the inner core of the cooling catheter of FIG. 8.

Within the inner core 44, as shown in FIGS. 10 and 16, the inner lumen 45 provides passage for interventional tools and a flow of cooled blood to an injured organ recovering from ischemia. Coolant lumen 46 carries coolant from the rear hub 26 down to the distal tip 31. Coolant lumen 47 carries a return flow of coolant from the distal tip 31 to the rear hub 27. The outer walls 48 and 50 that surround the coolant and blood flows respectively are configured to minimize heat transfer while maintaining a clinically acceptable overall outer diameter. The inner walls 49 and 51 are chosen to maximize and minimize heat transfer, respectively. Maximizing heat transfer between coolant flow and blood flow is counter balanced with the need ensure structural integrity as high pressure coolant, in the range of seven atmospheres, is circulated through the embodiment. Wall 51, a septum which separates the coolant lumen 46 from the coolant lumen 47, creates the bisected annulus and balances the design goal of minimizing heat transfer between delivered and returned coolant flows, and deflection as there relatively large temperature and force differentials occur across this wall These subtle features of the inner core 44 directly enable blood to be cooled continuously and delivered to injured organs as interventional tools are used.

Figure 11:
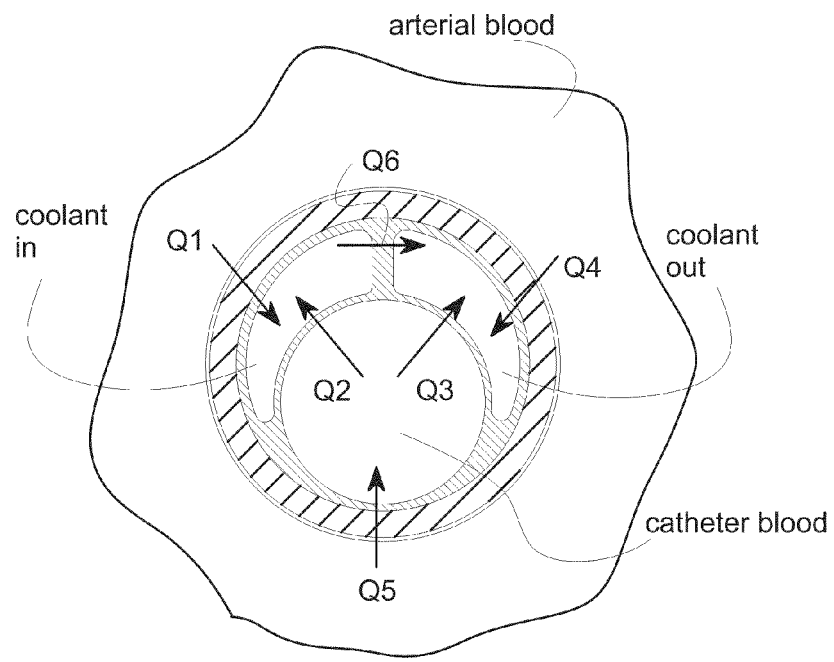
FIG. 11 is a representation of heat transfer across the boundaries of the cooling catheter as shown in FIG. 10.
Figure 12:
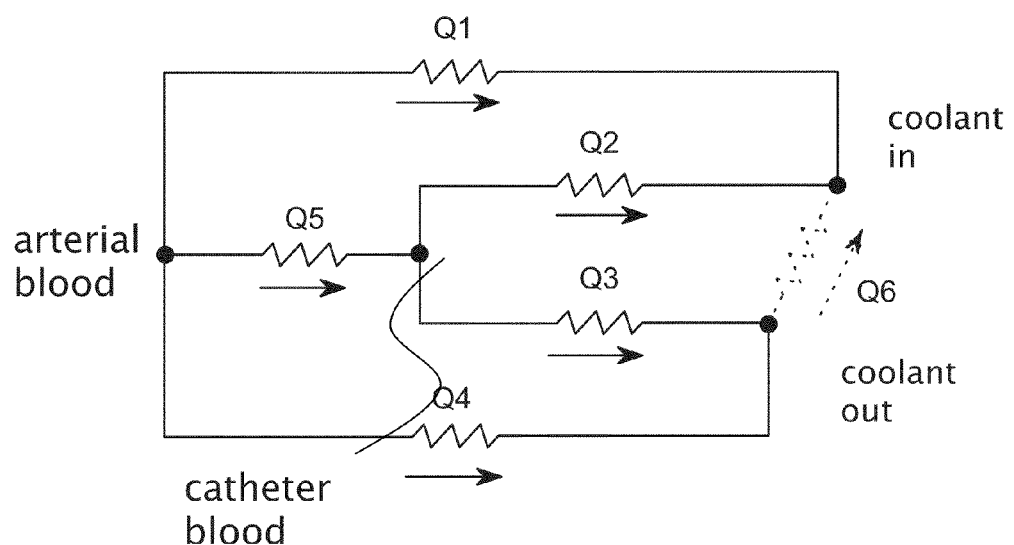
FIG. 12 illustrates a thermal circuit corresponding to FIG. 11.

To better understand these subtle features, understanding the heat transfer processes surrounding the inner core 44 is helpful; each is labeled Q1 through Q6 in FIGS. 11 and 12. Using FIG. 11 we can see that heat is transferred from warm arterial blood to the blood cooling catheter 22 in three different pathways: Q5 between arterial and catheter blood flow; Q1 between arterial blood flow and a coolant inlet flow in the coolant lumen 46; and Q4 between the arterial blood flow and the coolant outlet flow in the coolant lumen 47. Since the intent of this embodiment is to cool blood in the inner lumen 45, wall thicknesses and insulating properties are chosen to limit this heat transfer from warm blood to either cooled blood or coolant. Internally there are three more heat transfer pathways: Q2 between the catheter blood flow and the coolant inlet flow; Q3 between the catheter blood flow and coolant outlet flow; and Q6 between the coolant inlet flow and the coolant outlet flow across the septum wall 51. Again, when the design intent of this embodiment is considered, it is preferential to augment Q2 and Q3 with thin and/or conductive materials and reduce Q6 with thicker and/or potentially less conductive (insulating) materials.

Each of these heat transfer pathways is further illustrated in FIG. 12, as an equivalent thermal circuit. The inner core embodiment shown in FIG. 10 is configured to maximize Q2 and Q3, and to minimizes Q5, Q1, Q4, and Q6 within the manufacturing, clinical, and structural requirements of the catheter assembly.

Figure 13:
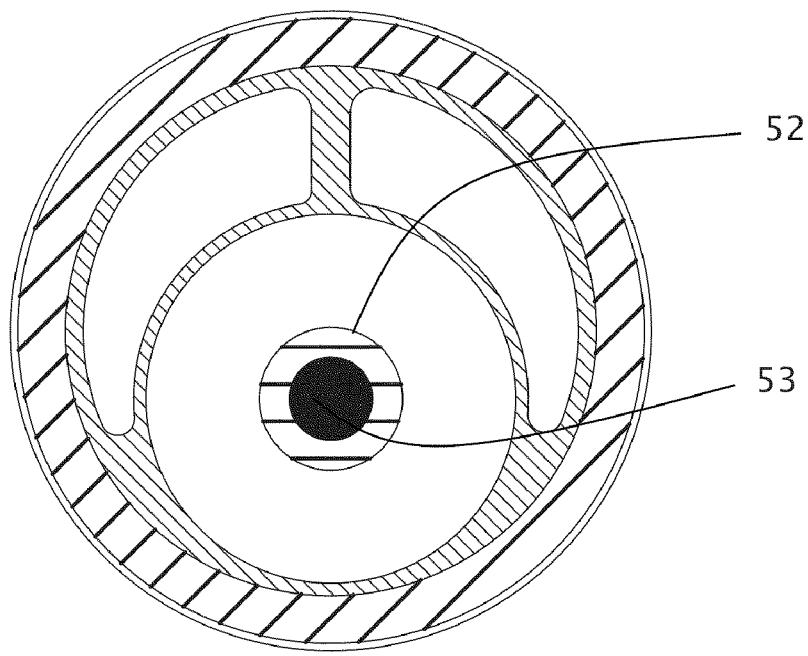
FIG. 13 shows the placement of a typical dilation catheter within an inner lumen of a cooling catheter of the present disclosure.

Fluid flow is directly coupled with heat transfer. Insufficient flow leads to insufficient heat transfer, as well as to potentially limiting blood flow below a critical ischemic threshold. During use, interventional tools, such as dilation catheter 52 are passed through the inner lumen 45 of the cooling catheter, such as shown in FIG. 13, illustrating to scale the relative size and position of a typical dilation catheter 52 that has a 0.024 inches (0.61 mm) outer diameter inside an inner lumen 45 with an inner diameter of 0.062 inches (1.575 mm). The dilation catheter itself is inserted over a guide wire 53 for accurate placement across a lesion of a diseased artery. Because of the substantial annular cross-sectional area between the deflated and wrapped dilation balloon catheter 52 and the interior of the inner core 44 blood flow resistance is minimized and continuously cooled blood perfusion can take place during an interventional procedure.

Figure 14:
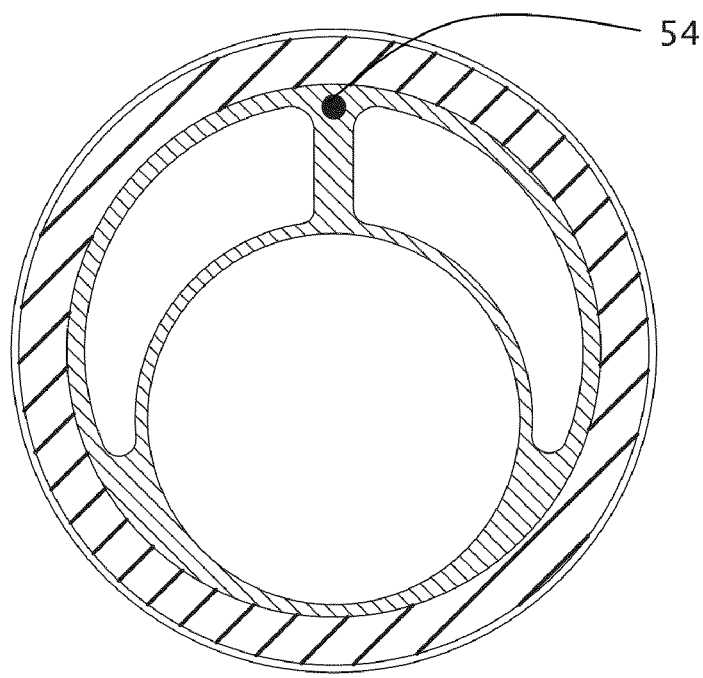
FIG. 14 illustrates placement of a thermocouple for measuring distal tip temperatures in the cooling catheter of the present disclosure.

During existing interventional procedures heart function is monitored carefully. The additional use of the preferred embodiment would enable close monitoring of delivered blood temperature. Temperatures at the distal tip 31 of the catheter 22 are monitored by a thermocouple wire 54 as shown in FIG. 14. Preferably, data from the thermocouple wire 54 is calibrated under controlled conditions to create correlations between observed tip temperatures and delivered blood temperatures for accurate control of cooled blood delivery.

Figure 15:
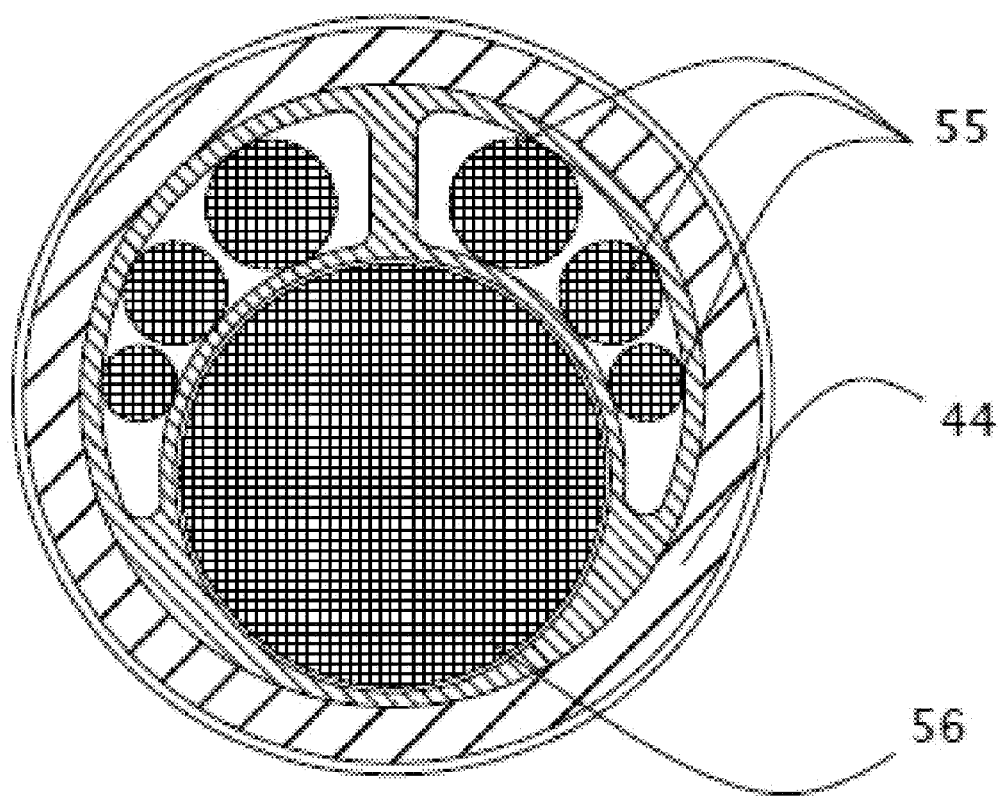
FIG. 15 illustrates the placement of mandrels used during application of braiding and exterior coating to the non-circular inner core of the cooling catheter shown in FIG. 10.

During assembly of the catheter 22, and in particular, during the application of the braiding 43 over the inner core 44, it is necessary to provide temporary internal support to prevent collapse. FIG. 15 illustrates the placement of Teflon-coated stainless steel interior mandrels 55 within the passages of the inner core 44 during application of the braiding 43 and the exterior coating 42 to the non-circular inner core 44. This support is needed because as the braiding is installed, radial forces are applied. These forces arise from two sources: a) applying the braiding itself to the outside of the inner core 48; and b) applying the external polymer 42, which is applied in a constricting fashion similar to heat shrink packaging. A plurality of coolant lumen mandrels 55 having different diameters, together with one central lumen mandrel 56 are placed inside the inner core 44 to prevent collapse. During braiding, radial forces are applied as the braid is tightly woven along the axis of the inner lumen core 44. If the inner core 44 is not supported by mandrels, these radial forces will crush the inner core. Typical mandrels include 0.007 inches, 0.010 inches, and 0.014 inches by 70 inches long, made of Teflon coated stainless steel. Typical braiding is 0.001 inch by 0.006 inch stainless steel flat braid wire.

Figure 17:
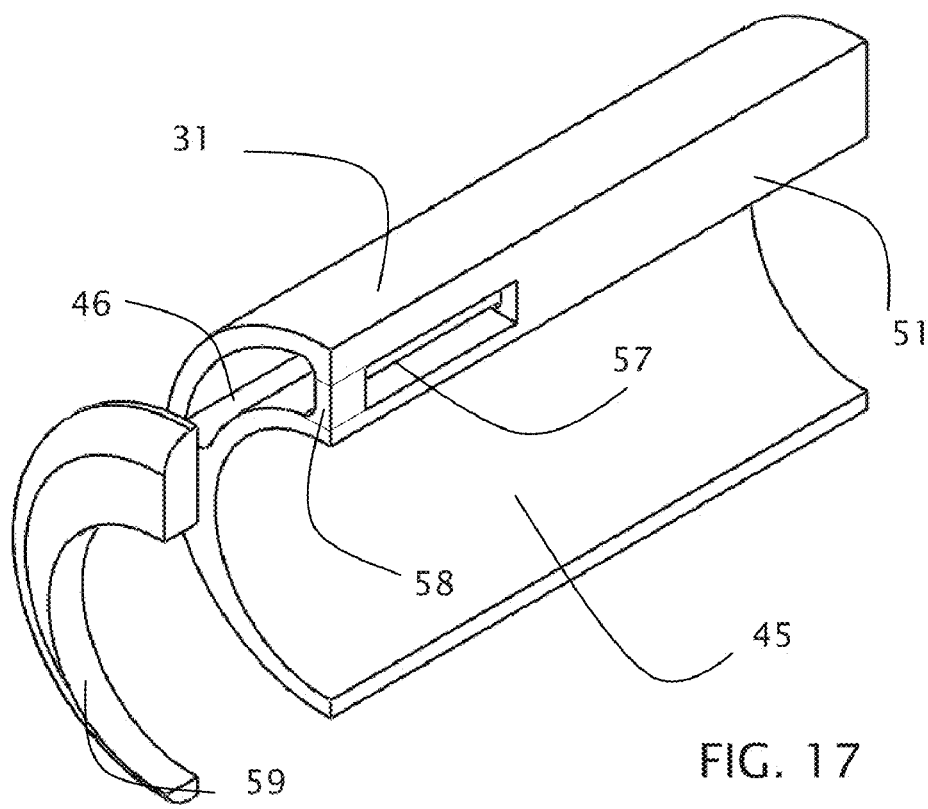
FIG. 17 is an isometric cross-sectional view along the axis of the cooling catheter of FIG. 8, at the distal tip.

At the distal tip 31 of the catheter 22, the inner lumen core 44 is configured to permit a flow of coolant to pass from the first coolant lumen 46 into the coolant return lumen 47 via a slot 57 disposed in the septum 51, as best seen in FIG. 17. The distal tip 31 is formed by laser or mechanically cutting a slot into the septum 51 and sealing the axial end of the distal tip with a Teflon™ adhesive such as Loctite 7701™, Loctite 3972™, or Loctite 4307™, after first treating the material with Loctite 7701™ primer. A polymer cap 59 is then used to seal the coolant pathways and allow blood flow and interventional tool passage through the inner lumen 45.

Figure 18:
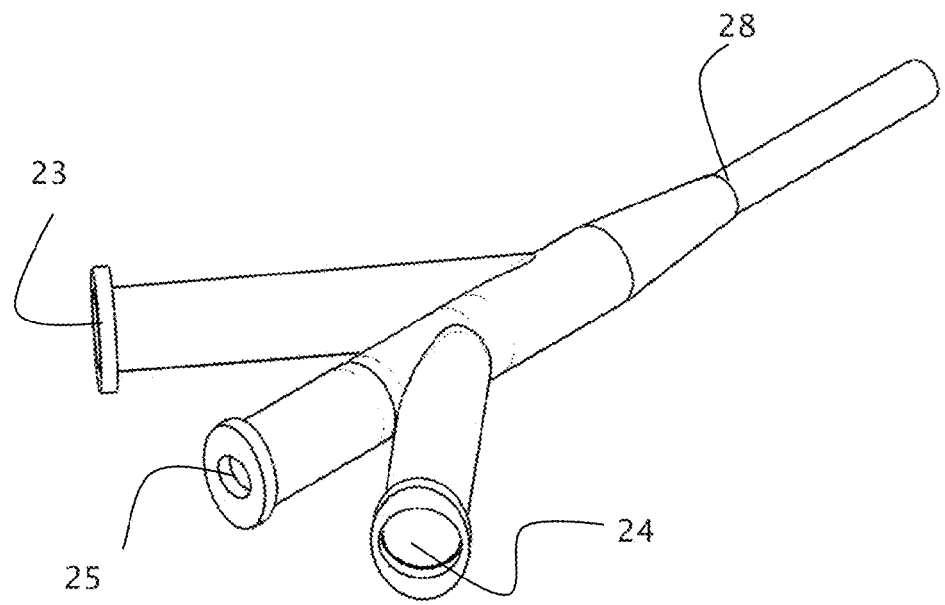
FIG. 18 shows an isometric view of the rear proximal hub assembly of the cooling catheter of FIG. 8.
Figure 19:
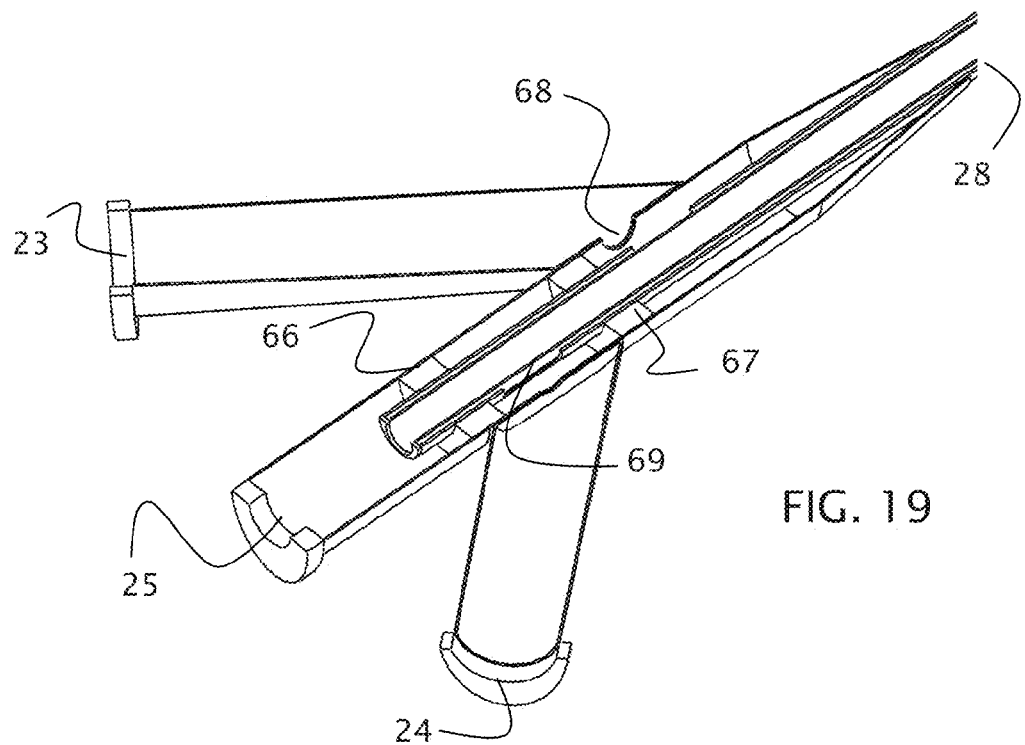
FIG. 19 is a cross-sectional view of the rear proximal hub of FIG. 18, taken in the horizontal plane.
Figure 20:
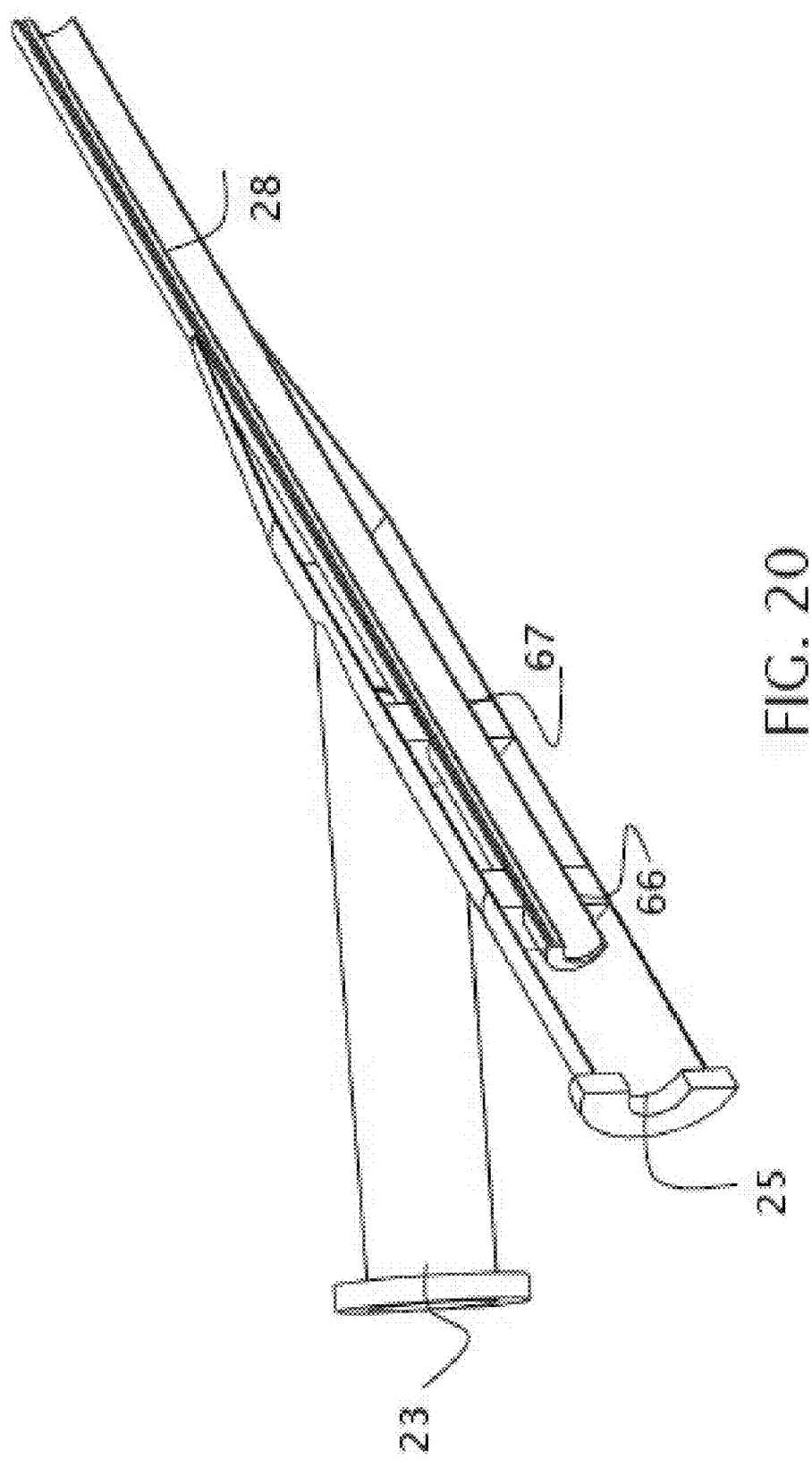
FIG. 20 is a cross-sectional view of the rear proximal hub of FIG. 18, taken in the vertical plane.

FIGS. 18 through 20 illustrate isometric and cross-sectional views along the shaft of the catheter at the proximal hubs 26 and 27, which are integrally formed into a molded rear hub. As best seen in FIGS. 19 and 20, a collar 66 is employed in the proximal hub to isolate the blood flow and interventional tools from the coolant inlet flow introduced via port 24. Preferably, the inlet coolant flow must enter the cooling catheter from the rearmost port position to avoid restricting the return coolant flow, which can be restricted when the high pressure coolant entering the coolant lumen 46 deflects the septum 51, limiting or blocking the return coolant flow in the adjacent coolant return lumen 47. By placing this high pressure region downstream of the returning coolant, the initial deflection blockage is avoided as the coolant exists the catheter 22. A second collar 67 isolates the inlet coolant flow entering the port 24 from a return outlet coolant flow exiting via port 23. Penetration holes 68 and 69 enable coolant to enter and exit the cooling catheter shaft coolant lumens. Finally a strain relief 28 ensures that rear hub to shaft kinking is minimized. This is particularly important since proper placement during angioplasty requires some device rotation and pushing to properly position the catheter.

Figure 26:
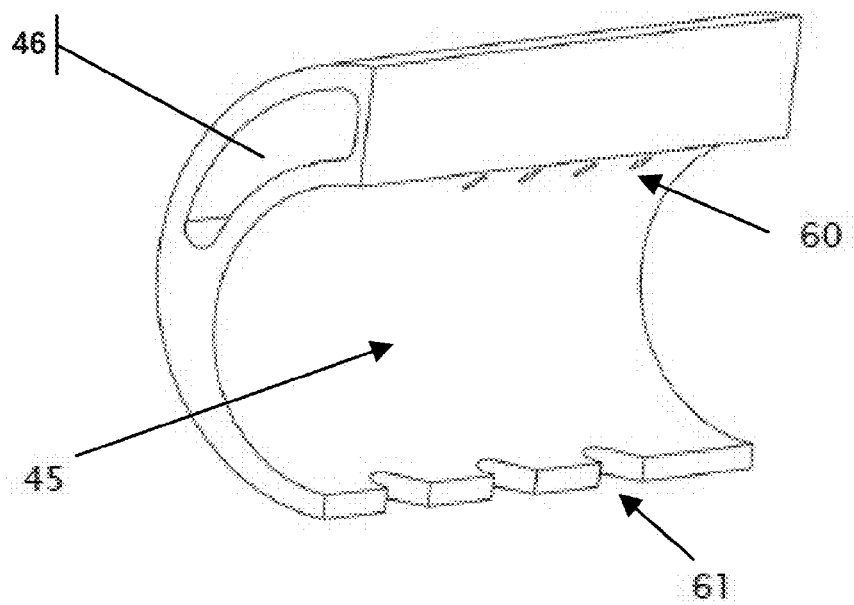
FIG. 26 is a cross-sectional isometric view of a cooling catheter incorporating blood entry holes.
Figure 27:
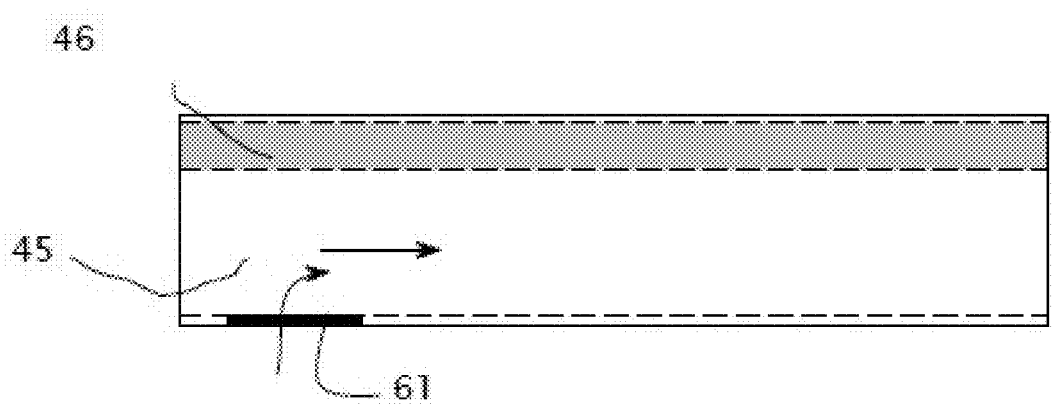
FIG. 27 is a side view schematic of blood flow into the cooling catheter of FIG. 26 via blood entry holes.
Figure 31:
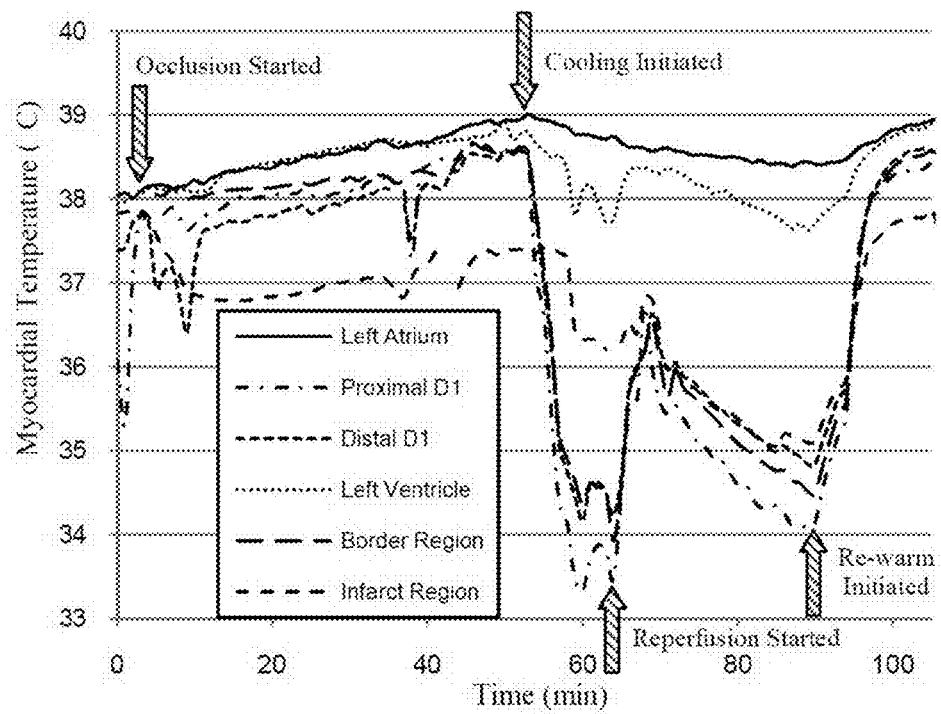
FIG. 31 is a plot of myocardial temperature versus time during experimental testing.

In an alternative embodiment of the catheter 22, shown in FIGS. 26-30 the rear proximal hub 25 is no longer employed to introduce blood into the catheter shaft 29, and a flow of liquid coolant is permitted to enter directly into the flow of blood in the inner lumen 45. FIGS. 26 and 27 show isometric and cross-sectional a side view schematic of blood flow into the catheter via one or more blood entry holes 61 that are laser or mechanically drilled through the outer coating 41, through the braid 43, and finally through the lower wall 50 of the inner core. FIG. 28 shows a top view schematic of blood flow into the catheter accompanied by infusion of coolant through infusion holes 60 as the blood travels towards the distal tip 31 along the inner lumen 45. FIG. 29 is similar to FIG. 27 except that the infusion holes 60 are more numerous. In addition the arrows representative of coolant flow in FIG. 29 are smaller, with a reduction in size reflecting a reduction in the amount of coolant infused.

In this alternate embodiment, blood is introduced into the inner lumen 45 through the blood entry holes 61. In addition coolant infusions holes 60 from the coolant lumens 46 and 47 into the inner lumen 45 are provided, and used to increase cooling capacity and decrease fluid shear drag along the inner walls of 45, as illustrated in FIG. 30.

These coolant infusion holes 60 are angled in the direction of blood flow relative to the central axis of the catheter 22, and can be made in several different ways: 1) micro drill bit and end mills ranging in size from 0.1 to 0.2 mm, 2) heated needles, and 3) eximer lasers. Eximer laser, for example, can make holes down to the micrometer level, 1/1000 of a millimeter. Lasers can be used to make the surface of the inner lumen 45 essentially porous such that coolant weeps from the coolant pathway into the blood pathway forming a thin lower viscosity cylinder that reduces shear stress at the inner lumen 45 wall allowing blood to flow more easily with less pressure differential. In the case of micro drill bits, holes are drilled through the out wall of the inner core 42, 43 (FIG. 10) and sealed with adhesive.

Figure 25:
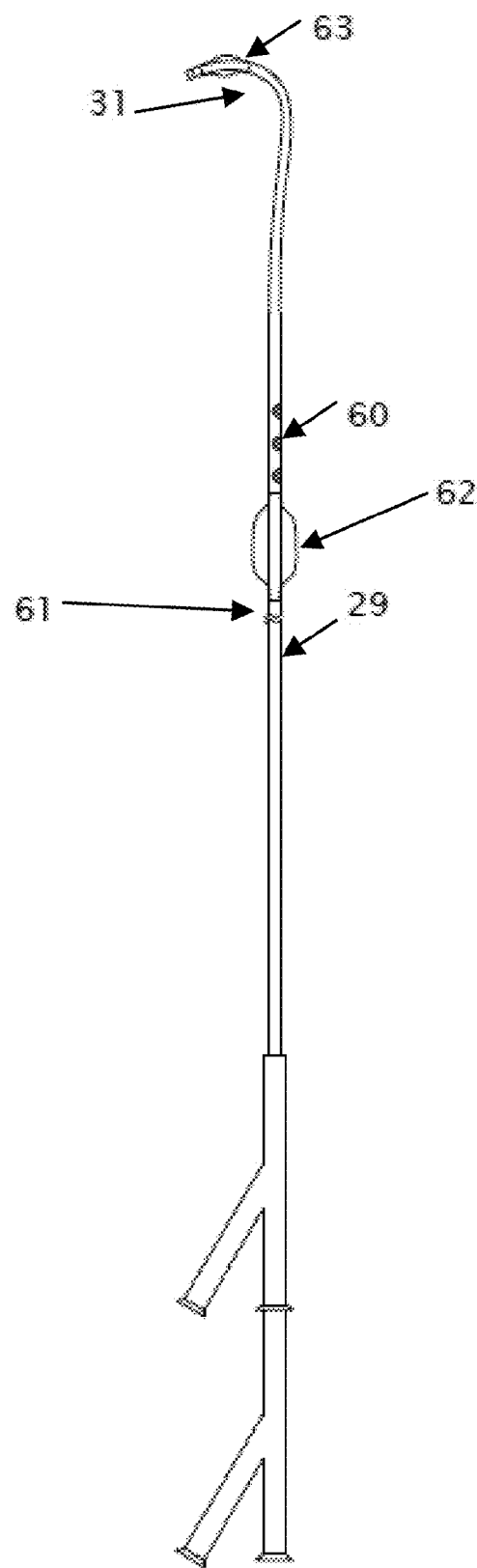
FIG. 25 is a complete catheter assembly configured to harnesses the natural blood pressure difference existing between the aorta and a smaller artery leading directly to an organ.

FIG. 25 shows an alternative embodiment of a complete catheter assembly 61, employing the configuration shown in FIGS. 26-30, configured to harness a natural blood pressure difference existing between the aorta and a smaller artery leading directly to an organ. Using one or two balloons 62, 63, located adjacent to either the proximal or distal ends of the catheter shaft 29, an increase in differential pressures between the ends of the catheter is formed when place within a patient to motivate a blood flow from blood entry holes 60 to the distal tip 31. The proximal balloon diameter would range in size from 10-20 mm, while the distal balloon diameter would range in size from 3-6 mm. The proximal balloon length would range in size from 2-5 cm, while the distal balloon length would range in size from 0.5 cm to 3 cm.

Figure 21:
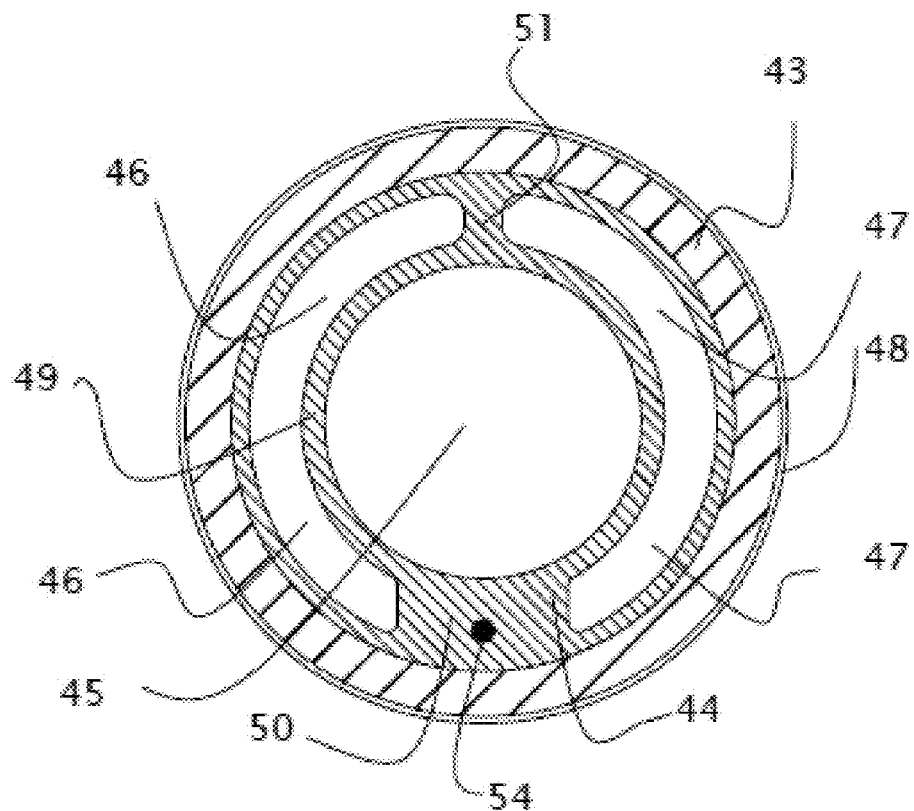
FIG. 21 is a cross-sectional view of an alternate embodiment of the cooling catheter of the present disclosure, defining a bisected concentric annulus.
Figure 22:
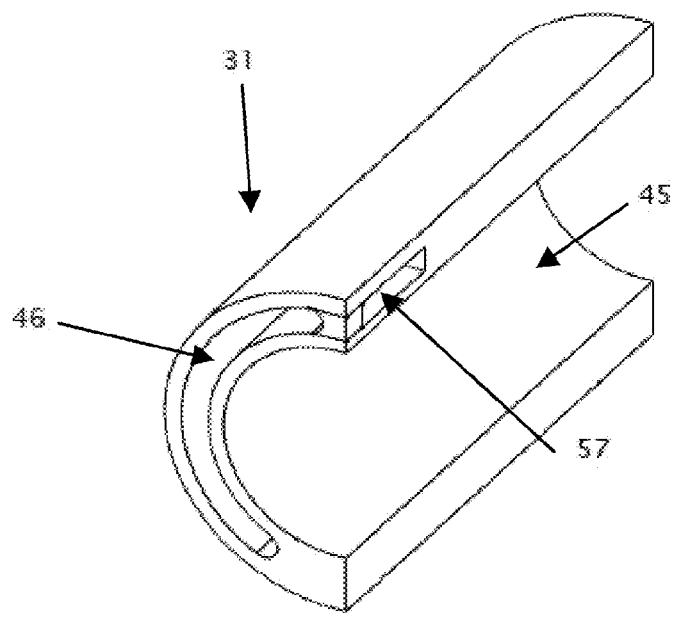
FIG. 22 is an isometric view of the inner core of the cooling catheter of FIG. 21.
Figure 23:
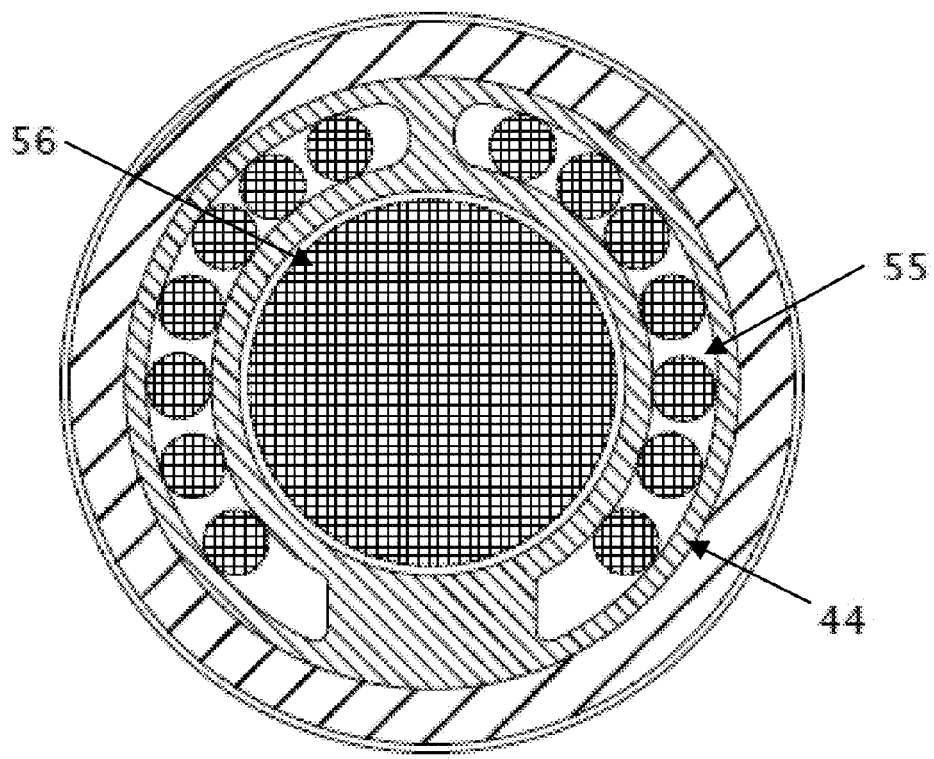
FIG. 23 illustrates the placement of mandrels used during application of braiding and exterior coating to the non-circular inner core of the cooling catheter shown in FIG. 21.

Those of ordinary skill in the art will recognize that the design considerations shown in FIG. 7 for the configuration of the inner core of the catheter shaft 29, do not necessarily restrict the cross-sectional configuration to that shown in FIG. 10. For example, as seen in FIGS. 21 through 23, an alternative embodiment of the inner core 44 can be constructed with suitable mandrels 55 and 56 which provides a cross-sectional view is no longer a bisected eccentric annulus, but instead consists of a bisected concentric annulus which provides substantially the same features. With the alternate configuration shown in FIGS. 21 and 22, the coolant lumens 46, 47 more fully cover or encompass the central blood pathway 45. This geometric difference attempts to reduce the heat transfer vector Q5, shown in FIGS. 11 and 12 The same distal tip configuration of caps and seals is used to allow coolant flow to travel from the inlet pathway 46 to the exit pathway 47. Using a slot 57 cut into the septum 51 coolant travels to the distal tip 31 and returns to the proximal hub 26, as best seen in FIG. 22.

Figure 24:
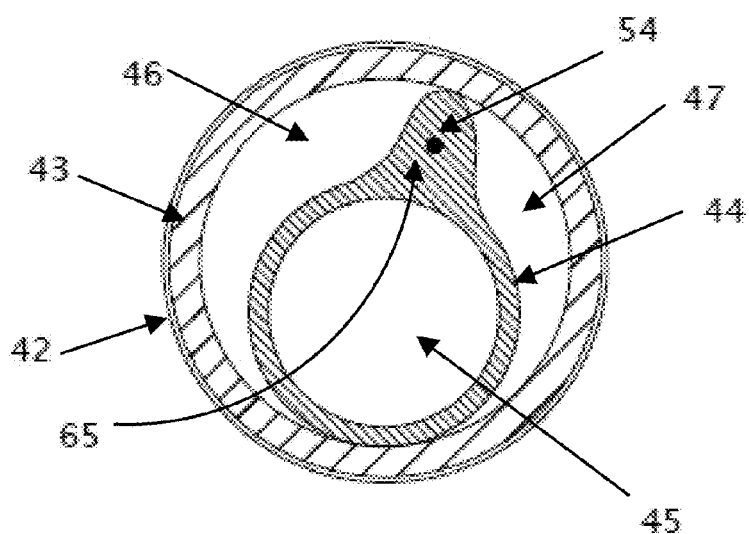
FIG. 24 is a cross-sectional view of another alternate embodiment of the cooling catheter of the present disclosure.

Yet another embodiment is shown in FIG. 24, which provides a simpler extrusion compared to the embodiments previously shown in FIGS. 10 and 21. Each of the features previously identified in FIGS. 10 and 21 remains also present in FIG. 24. In this alternative embodiment a non-circular inner core extrusion 44 is placed inside circular extrusion. Braiding 43 and an exterior wall 42 are applied as in the previous embodiments. High pressure coolant inlet flow in the lumen 46 forces the non-circular inner lumen to tilt away from the high pressure side and towards the lower pressure coolant return pathway in lumen 47. In addition to those features, FIG. 24 shows an additional lumen 65 that may allow a conduit to a thermocouple wire, a guide wire, or another interventional tool.

Operation

In a clinical setting the preferred embodiment of the cooling catheter 22 is used in the identical fashion as a standard guide catheter during emergency angioplasty. Using and introducer sheath 41, together with a conventional fluoroscopy system (not shown) found in catheter laboratories, the cooling catheter 22 is first guided into the ostium of the coronary artery of interest within a patient. Once the cooling catheter 22 has engaged the ostium, there are two approaches possible for motivating blood flow through the cooling catheter. In a first embodiment, an external pump, such as a peristaltic pump 39, can be used. In a second embodiment, employing one or more blood entry holes 61 in the cooling catheter shaft 29, the natural differential pressure between the aorta and smaller artery may auto-perfuse blood flow through the cooling catheter. Using auto-perfuse techniques, blood is able to flow without energy input from an external pump, traveling from blood entry holes 61 to the distal tip 31. The amount of blood flow is proportional to four factors: the blood viscosity, the diameter of the inner lumen, the distance the blood must travel within the cooling catheter shaft 29, and the differential pressure between the aorta and the ostium. Medical research indicates that the differential pressure between the aorta and the ostium can range from 3-50 mmHg. With inner lumen diameters of 1.2 to 1.8 mm, these natural differential pressures enable blood flow rates ranging from 20 to 100 ml/min when blood entry holes 61 are 20-40 cm from the distal tip 62.

To cool the blood that enters and travels inside the cooling catheter 22, cooled surfaces in contact with the flow of blood are required. These surfaces draw heat away from the blood as it travels inside the cooling catheter, as indicated by heat transfer vectors Q2 and Q3, shown in FIGS. 11 and 12. The coolant is circulated through the coolant pathways or lumens 46 and 47 found in the cooling console 33. Coolant pumps, located in a console 33 outside the patient, pump coolant in a closed loop between a warm patient and a cold heat exchanger. The heat exchanger is maintained at a colder temperature of about 2 degrees Celsius by a standard laboratory chiller, such as Thermo Electron Corporation, Portsmouth, N.H. USA, and Model M25. To ensure maximum cooling, the laboratory chiller, using its own internal chiller pump, pumps fluids at 3-4 liters per minute, can use fluids such as propylene glycol mixtures with freeze points as low as −20 C. The chiller pump moves fluid at flow rates ranging from 100-500 ml/min through the console 33 heat exchanger. A recirculation loop in the coolant pathway is used to ensure the maximum velocities through the console 33 heat exchanger (not shown) to maximize heat transfer performance. So while the catheter coolant flow rates are significantly lower 30-150 ml/min, the heat exchanger receives much higher chiller flow rates to minimize the chiller-side heat transfer resistances.

With the cooling catheter in place and coolant pumping within it, blood exits from the distal tip 31 of the catheter and enters the organ of interest, primarily the heart or brain. At the same time this is occurring, a physician uses the inner lumen or interventional pathway 45 to carry out other interventional tasks. The physician uses the tools similar to those described in FIGS. 5-6 to open diseased arteries and try to maintain blood flow after the catheter procedure. By using a guide catheter based platform for organ-specific cooling, the physician makes only one arterial penetration to reduce ischemic and reperfusion tissue damage and carry out interventional work, such as angioplasty and stent placement. Upon completing the interventional procedure of interest, the physician can either remove the catheter or leave it in place to maintain cooled blood reperfusion for extended periods of hypothermia tissue protection.

To ensure that adequate tissue cooling occurs the blood flow heat transfer challenge involves maximizing heat transfer inside minimum volume or size. In other words heat transfer enhancement is the fundamental task for achieving safe, effective arterial cooling. Heat exchanger design optimization attempts to achieve one or a combination of the following objectives: 1) reduce the size of the transport device, 2) increase the UA (U, the overall transport coefficient and A, the exchange surface area) to increase the heat and or mass exchange rate, and 3) reduce the pumping power required to meet a heat and/or mass exchange target value. These objectives are also carefully balanced against clinical, manufacturing, and structural requirements illustrated in FIG. 7.

In addition to convective heat transfer by cold surfaces, blood flowing through the cooling catheter 22 may alternatively be directly cooled by cold infusion to reduce blood temperature within the cooling catheter, by employing the alternative configurations shown in FIGS. 26-30. FIG. 28 shows a cross-section of the alternate configuration of the cooling catheter 22 with one or more blood entry holes 61. This alternative embodiment no longer uses the rear proximal hub 25 to introduce blood into the catheter. Instead blood is introduced through the holes 61 that are laser or mechanically drilled through the outer coating 41, through the braid 43, and finally through the lower wall 50 of the inner core. Blood enters the central lumen 45 through these holes 61, and travels towards the lower pressure distal end 31. Along the way the blood is cooled along a cooled inner surface wall 45. In addition, coolant passes through the infusion holes 60 from the coolant lumen 46 into the central lumen 45 due to the pressure difference between the coolant pumping pressure and the internal blood pressure. These infusion coolant holes may vary in terms of hole size, angle of penetration, number of holes, and hole array configuration. For example, FIG. 29 shows an array of angle coolant infusion entry holes. FIG. 30 shows these holes in relation to a developing hydrodynamic boundary layer, where the design intent of infusion is to increase cooling capacity while decreasing fluid drag since the coolant is typically isotonic saline solution, to ensure safety, and its viscosity is roughly one third that of blood.

Coolant infusion enhances cooling catheter performance in two fundamental ways, by mixing and exchanging momentum. The first benefit from mixing occurs when the coolant mixes with the blood and comes to cooler equilibrium temperature. If the coolant infusion rates amount are small relative to the blood flow rates and the coolant enters at 4° C., each ml/min of infusion has the potential to cool the blood flowing inside the cooling catheter by approximately 2.3 Watts. The second benefit from mixing is reduced viscosity. This reduction in viscosity enables greater flows inside the blood lumen 45 for equivalent diameters, lengths, and pressure differences. If the coolant chosen is isotonic saline solution (0.9% sodium chloride), a typical infusion fluid, the viscosity is approximately one-third that of blood. Mixing this fluid with blood dramatically reduces the bulk fluid viscosity. Finally, the entering infusion is angled in the direction of blood flow enabling momentum exchange towards the distal tip of the cooling catheter.

The operation of this hybrid infusion—surface cooling catheter is nearly identical to the operation of the preferred embodiment described previously. The only difference in operation is the coolant circulation control. To control infusion rates, coolant pumping pressures are monitored with typical pressure transducers (not shown) in the coolant pumping circuit. Furthermore, the amount of infused coolant is directly monitored by either circuit flow meters or coolant reservoir volume monitors.

Experimental Results

The cooling catheter 22 and method of the invention has been utilized to acquire experimental data in the following examples using 65-75 kg swine. In substantially the same manner as a standard guide catheter, the distal tip of the cooling catheter 22 was placed in the right or left main coronary artery of the swine. When the distal tip is in place, cooled blood flows through the cooling catheter and warm blood flows around the catheter in the annulus formed between the catheter outer wall and vessel inner wall. All animal use was approved by the Office of Laboratory Animal Welfare Large swine (65-75 kg.) underwent a non-survival ischemia-reperfusion study. Six type-T thermocouple probes (Physitemp, Clifton, N.J.) were inserted 2 cm into myocardial tissue locations: left atrium, proximal and distal main branch of the LAD (D1), lateral left ventricle (LV), border and ischemic regions. To initiate ischemia, silk snares were placed around a distal region of the left anterior descending (LAD) coronary artery. The vessel was occluded for a total of 60 minutes. At 45 minutes into the 60 minute occlusion, the cooling catheter 22 was inserted into the left main coronary artery with the tip of the catheter positioned slightly into the main proximal LAD to direct cooled blood flow proximal to the occlusion. Ten minutes before reperfusion, cooled blood delivery was initiated. Cooling was continued for 25 minutes following reperfusion. A step-wise controlled re-warming was conducted for 5 minutes and then the catheter was removed. Animals were reperfused for a total of 3 hours. Control animals were similarly treated using normothermic blood pumping conditions.

To assess area at risk (AAR) and infarct size (IS), the heart was double stained with Evans Blue dye and TTC. Using planimetry, the IS and AAR were measured as a percentage of the left ventricle and the IS/AAR was calculated. Statistical significance between the two groups was determined using a Student's T-test with $p<0.05$.

Figure 32:
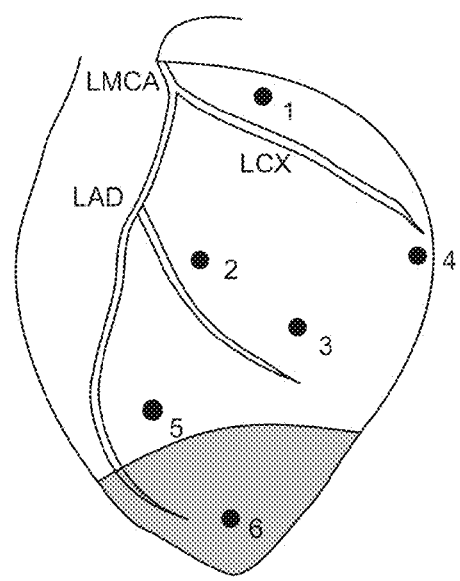
FIG. 32 illustrates temperature measurement locations on an animal heart during experimental testing.

A total of 11 animals were used in the study, and six successfully completed the test protocol. Of the six animals, four received hypothermic therapy and two, normothermic reperfusion. Temperature measurement locations were the following: #1 the left atrium, #2, the proximal D1, #3 distal D1, #4 the left ventricle, #5 the border zone, and #6 the infarct region, as shown in FIG. 32. Myocardial tissue temperature drop in the infarct region was 3±1.1° C. with little systemic cooling (FIG. 32), indicated by left atrium cooling. The border zone or pneumbra lies in the region immediately adjacent to the infract region or ischemic core. The border zone is where tissue is potential salvageable.

Figure 33:
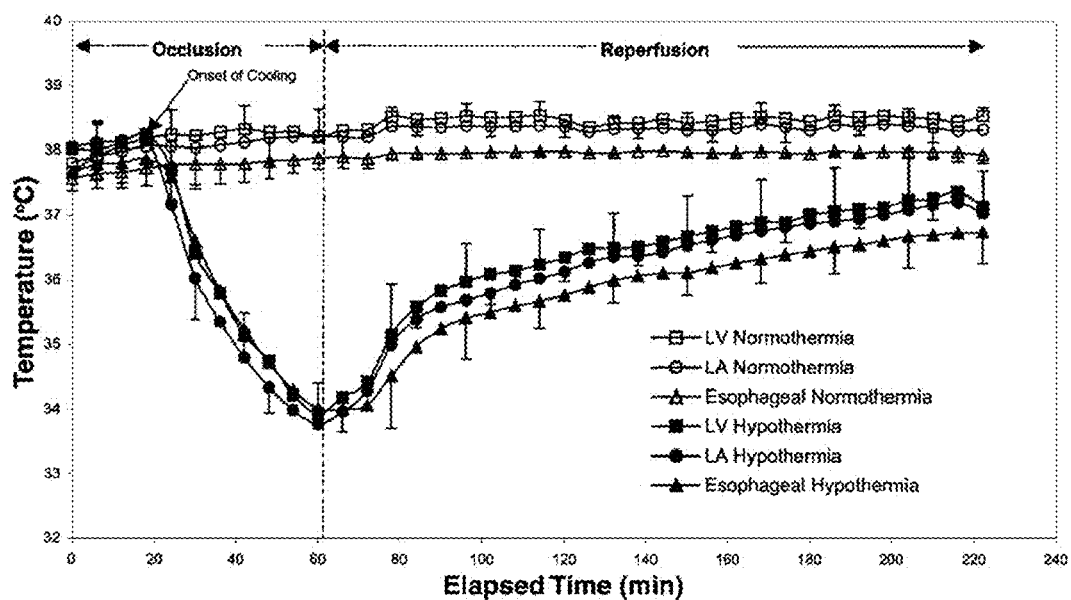
FIG. 33 is plot of temperature versus time during experimental testing.

Comparing these cooling rates to established whole-body cooling catheters, FIG. 33. reveals a dramatic difference in tissue temperature behavior. In typical invasive whole body cooling devices FIG. 33. the entire body is cooled at rate of approximately 0.1 degree Celsius per minute. This is contrast to localized organ cooling that is achieved with preferred embodiment, approximately 0.7 degrees Celsius per minute.

Taking a closer look at the ability of cooled reperfusion to reduce tissue damage arise from ischemia and subsequent reperfusion injury the AAR as a function of LV were the same size for hypothermic treatment (16.7±1.7%) and control (16.5±0.1%) groups. However, infarct size as a percent of AAR showed a significant reduction of approximately 51% for hypothermic treatment compared to normothermic controls (24.3±13.2 compared to 49.8±2.0, p=0.06).

As various changes could be made in the above constructions without departing from the scope of the disclosure, it is intended that all matter contained in the above description or shown in the accompanying drawings shall be interpreted as illustrative and not in a limiting sense.

The invention claimed is:

1. A catheter for the treatment of reperfusion injury by locally cooling blood in an internal blood-conveyance pathway and permitting an interventional tool to pass through the internal blood-conveyance pathway while blood is flowing to perform interventional treatment, the cooling catheter comprising:
    a flexible shaped catheter shaft configured to be inserted into a blood vessel of a patient, having a proximal end and a distal end, said catheter shaft having an inner core defining an inner blood conveyance lumen, a first coolant lumen having an arcuate cross-section in thermal contact along an axial length of a first peripheral wall region of said inner blood conveyance lumen, and a second coolant lumen having an arcuate cross-section in thermal contact along said axial length of a second peripheral wall region of said inner blood conveyance lumen;
    wherein said first and second coolant lumen are in thermal contact with each other across a septum wall extending the length of the catheter shaft; and
    wherein said first and second coolant lumen are in fluid contact adjacent to said distal end of said catheter shaft through an interconnecting slot in said septum wall, whereby coolant flow delivered to said first coolant lumen is discharged from said second coolant lumen.

2. The catheter of claim 1 wherein said septum wall is configured to minimize heat transfer between said first and second coolant lumen along said axial length of said catheter shaft.

3. The catheter of claim 1 wherein said septum wall is radially aligned within said inner core of said catheter shaft.

4. The catheter of claim 1 wherein said first and second coolant lumen each have a have a non-concentric configuration.

5. The catheter of claim 1 further including a composite outer wall enclosing said inner core.

6. The catheter of claim 5 wherein said composite outer wall includes reinforcing braiding embedded within a polymer.

7. The catheter of claim 5 wherein said outer composite wall is configured to minimize heat transfer from an exterior surface of said catheter shaft to said inner blood conveyance lumen, and to said first and second coolant lumen.

8. The catheter of claim 1 wherein said first and second coolant lumen are integrally formed with said inner blood conveyance lumen within said inner core, and wherein said inner core is configured to maximize thermal transfer from said inner blood conveyance lumen into said first and second coolant lumen across said first and second peripheral wall regions.

9. The catheter of claim 1 wherein said inner blood conveyance lumen is eccentrically disposed within said inner core.

10. The catheter of claim 1 wherein said first and second coolant lumen are enclosed at said distal end of said catheter shaft; and
    wherein said inner blood conveyance lumen is open at said distal end of said catheter shaft.

11. The catheter of claim 1 further including a thermocouple disposed within said septum wall, adjacent to said distal end of said catheter shaft, said thermocouple configured to measure a temperature of blood flow within said catheter shaft.

12. The catheter of claim 1 further including a hub member coupled to a proximal end of said catheter shaft.

13. The catheter of claim 12 wherein said hub member includes at least an infusion inlet in fluid communication with said first coolant lumen to deliver a flow of coolant; and
    at least an infusion outlet in fluid communication with said second coolant lumen to receive a return flow of said coolant;
    wherein said infusion inlet is proximally located along said hub member relative to said infusion outlet.

14. The catheter of claim 12 wherein said hub member includes at least one access port in communication with said inner blood conveyance lumen for the passage of an interventional tool through said catheter shaft via said inner blood conveyance lumen.

15. The catheter of claim 1 further including an introducer sheath in fluid communication with said inner blood conveyance lumen, adjacent to a proximal end of said catheter shaft, said introducer sheath configured to provide a pathway for a flow of blood to enter said inner blood conveyance lumen.

16. The catheter of claim 1 further including at least one blood entry hole between said inner blood conveyance lumen and an exterior surface of said catheter shaft, displaced from said distal end of said catheter shaft, said blood entry hole providing a pathway for a flow of blood to enter said inner conveyance lumen.

17. The catheter of claim 1 further including a plurality of infusion holes within said first limited peripheral wall region between said first coolant lumen and said inner blood conveyance lumen, displaced from said distal end of said catheter shaft, whereby a flow of coolant from within said first coolant lumen is infused into said blood conveyance lumen.

18. The catheter of claim 17 wherein each of said plurality of infusion holes is directionally aligned towards said distal end of said catheter shaft.

19. The catheter of claim 17 wherein said plurality of infusion holes are disposed to introduce said flow of coolant into said blood conveyance lumen to form a hydrodynamic boundary layer within which a flow of blood is directed.

20. The catheter of claim 1 further including at least one inflatable balloon member concentrically disposed about an exterior surface of said catheter shaft, displaced from said distal end.

* * * * *